(12) United States Patent
Dar et al.

(10) Patent No.: US 8,738,137 B2
(45) Date of Patent: May 27, 2014

(54) SYSTEM FOR TRANSMITTING ELECTRICAL CURRENT TO A BODILY TISSUE

(75) Inventors: Amit Dar, Kfar Hess (IL); Shai Feldman, Kfar Saba (IL); Arkady Glukhovsky, Santa Clarita, CA (US); Shmuel Springer, Modi'in (IL); Einan Regev, Kefar Vradim (IL)

(73) Assignee: Bioness Inc., Valencia, CA (US)

( * ) Notice: Subject to any disclaimer, the term of this patent is extended or adjusted under 35 U.S.C. 154(b) by 88 days.

(21) Appl. No.: 12/628,273

(22) Filed: Dec. 1, 2009

(65) Prior Publication Data

US 2010/0076533 A1    Mar. 25, 2010

Related U.S. Application Data

(63) Continuation-in-part of application No. 12/197,849, filed on Aug. 25, 2008, now Pat. No. 8,467,880.

(60) Provisional application No. 60/957,592, filed on Aug. 23, 2007.

(51) Int. Cl.
*A61N 1/18* (2006.01)

(52) U.S. Cl.
USPC ................. 607/45; 607/46; 607/115

(58) Field of Classification Search
USPC ............ 607/36–38, 46, 48–59, 77, 98–99, 607/108–115, 139–155
See application file for complete search history.

(56) References Cited

U.S. PATENT DOCUMENTS

| | | | |
|---|---|---|---|
| 3,835,864 | A | 9/1974 | Rasor et al. |
| 4,088,141 | A | 5/1978 | Niemi |
| 4,323,999 | A | 4/1982 | Yoshizawa et al. |
| 4,699,143 | A | 10/1987 | Dufresne et al. |
| 4,702,732 | A | 10/1987 | Powers et al. |
| 4,832,032 | A | 5/1989 | Schneider |
| 5,080,099 | A | 1/1992 | Way et al. |
| 5,097,833 | A | 3/1992 | Campos |
| 5,169,384 | A | 12/1992 | Bosniak et al. |

(Continued)

FOREIGN PATENT DOCUMENTS

| | | |
|---|---|---|
| DE | 4331945 A1 | 3/1995 |
| JP | 2005-237941 | 9/2005 |

(Continued)

OTHER PUBLICATIONS

Office Action for U.S. Appl. No. 11/867,454, mailed Mar. 2, 2011.

(Continued)

*Primary Examiner* — Rex R Holmes
(74) *Attorney, Agent, or Firm* — Cooley LLP

(57) ABSTRACT

In some embodiments, an apparatus includes a substantially rigid base and a flexible substrate. The substantially rigid base has a first protrusion and a second protrusion, and is configured to be coupled to an electronic device. The flexible substrate has a first surface and a second surface, and includes an electrical circuit configured to electronically couple the electronic device to at least one of an electrode a battery, or an antenna. The flexible substrate is coupled to the base such that a first portion of the second surface is in contact with the first protrusion. A second portion of the second surface is non-parallel to the first portion.

20 Claims, 23 Drawing Sheets

(56) References Cited

U.S. PATENT DOCUMENTS

| | | | |
|---|---|---|---|
| 5,246,418 A | 9/1993 | Haynes et al. | |
| 5,330,516 A | 7/1994 | Nathan | |
| 5,337,748 A * | 8/1994 | McAdams et al. | 600/396 |
| 5,356,428 A | 10/1994 | Way | |
| 5,387,189 A | 2/1995 | Gory et al. | |
| 5,397,338 A | 3/1995 | Grey et al. | |
| 5,465,715 A | 11/1995 | Lyons | |
| 5,487,759 A | 1/1996 | Bastyr et al. | |
| 5,514,165 A | 5/1996 | Malaugh et al. | |
| 5,562,707 A | 10/1996 | Prochazka et al. | |
| 5,578,065 A | 11/1996 | Hattori et al. | |
| 5,613,943 A | 3/1997 | Palumbo | |
| 5,674,261 A | 10/1997 | Smith | |
| 5,814,090 A | 9/1998 | Latterell et al. | |
| 5,879,322 A | 3/1999 | Lattin et al. | |
| 5,916,244 A | 6/1999 | Walters | |
| 5,948,006 A | 9/1999 | Mann | |
| 6,002,965 A | 12/1999 | Katz et al. | |
| 6,214,032 B1 | 4/2001 | Loeb et al. | |
| 6,282,448 B1 | 8/2001 | Katz et al. | |
| 6,377,848 B1 | 4/2002 | Garde et al. | |
| 6,438,428 B1 | 8/2002 | Axelgaard et al. | |
| 6,445,955 B1 * | 9/2002 | Michelson et al. | 607/46 |
| 6,564,102 B1 | 5/2003 | Boveja | |
| 6,629,968 B1 | 10/2003 | Jain et al. | |
| 6,668,191 B1 | 12/2003 | Boveja | |
| 6,735,474 B1 | 5/2004 | Loeb et al. | |
| 6,735,475 B1 | 5/2004 | Whitehurst et al. | |
| 6,754,472 B1 | 6/2004 | Williams et al. | |
| 6,840,919 B1 | 1/2005 | Håkansson | |
| 6,892,098 B2 | 5/2005 | Ayal et al. | |
| 6,896,675 B2 | 5/2005 | Leung et al. | |
| 6,928,320 B2 | 8/2005 | King | |
| 6,941,171 B2 | 9/2005 | Mann et al. | |
| 6,961,623 B2 | 11/2005 | Prochazka | |
| 6,997,735 B2 * | 2/2006 | Ehr et al. | 439/371 |
| 7,013,179 B2 | 3/2006 | Carter et al. | |
| 7,047,071 B2 | 5/2006 | Wagner et al. | |
| 7,096,064 B2 | 8/2006 | Deno et al. | |
| 7,146,210 B2 | 12/2006 | Palti | |
| 7,242,982 B2 | 7/2007 | Singhal et al. | |
| 7,324,853 B2 | 1/2008 | Ayal et al. | |
| 7,389,145 B2 | 6/2008 | Kilgore et al. | |
| 7,502,652 B2 | 3/2009 | Gaunt et al. | |
| 7,536,226 B2 | 5/2009 | Williams et al. | |
| 2002/0019652 A1 | 2/2002 | Da Silva | |
| 2002/0055761 A1 | 5/2002 | Mann et al. | |
| 2002/0151951 A1 | 10/2002 | Axelgaard et al. | |
| 2002/0193844 A1 | 12/2002 | Michelson et al. | |
| 2003/0028232 A1 | 2/2003 | Camps et al. | |
| 2003/0078642 A1 | 4/2003 | Malaney et al. | |
| 2003/0139794 A1 | 7/2003 | Jenney et al. | |
| 2003/0171792 A1 | 9/2003 | Zarinetchi et al. | |
| 2003/0181090 A1 | 9/2003 | Ehr et al. | |
| 2003/0199807 A1 | 10/2003 | Dent et al. | |
| 2003/0212395 A1 | 11/2003 | Woloszko et al. | |
| 2004/0130455 A1 | 7/2004 | Prochazka | |
| 2004/0176804 A1 | 9/2004 | Palti | |
| 2004/0199222 A1 | 10/2004 | Sun et al. | |
| 2004/0204686 A1 | 10/2004 | Porter et al. | |
| 2004/0220641 A1 | 11/2004 | Wagner et al. | |
| 2005/0070970 A1 | 3/2005 | Knudson et al. | |
| 2005/0136385 A1 | 6/2005 | Mann et al. | |
| 2005/0277841 A1 | 12/2005 | Shennib | |
| 2006/0064140 A1 | 3/2006 | Whitehurst et al. | |
| 2006/0206165 A1 | 9/2006 | Jaax et al. | |
| 2006/0271118 A1 | 11/2006 | Libbus et al. | |
| 2007/0060975 A1 | 3/2007 | Mannheimer et al. | |
| 2007/0088419 A1 | 4/2007 | Fiorina et al. | |
| 2008/0004676 A1 | 1/2008 | Osypka et al. | |
| 2008/0046053 A1 | 2/2008 | Wagner et al. | |
| 2008/0243216 A1 | 10/2008 | Zilberman et al. | |
| 2008/0288026 A1 * | 11/2008 | Cross et al. | 607/60 |
| 2009/0054952 A1 | 2/2009 | Glukhovsky et al. | |
| 2009/0177131 A1 | 7/2009 | Dar et al. | |
| 2009/0222053 A1 | 9/2009 | Gaunt | |
| 2009/0326602 A1 | 12/2009 | Glukhovsky et al. | |
| 2010/0016929 A1 | 1/2010 | Prochazka | |
| 2010/0198298 A1 | 8/2010 | Glukhovsky et al. | |
| 2013/0138164 A1 | 5/2013 | Dar et al. | |

FOREIGN PATENT DOCUMENTS

| | | |
|---|---|---|
| JP | 2009-10003 | 1/2009 |
| WO | WO 95/10323 | 4/1995 |
| WO | WO 01/03768 A1 | 1/2001 |
| WO | WO 02/02182 A2 | 1/2002 |
| WO | WO 2006/101917 A2 | 9/2006 |
| WO | WO 2006/113654 A1 | 10/2006 |
| WO | WO 2006/113801 A2 | 10/2006 |
| WO | WO 2008/140242 A1 | 11/2008 |
| WO | WO 2009/058258 A1 | 5/2009 |
| WO | WO 2011/068849 | 6/2011 |

OTHER PUBLICATIONS

Supplementary Search Report for European Patent Application No. 08827776.9, mailed Mar. 10, 2011.
Office Action for U.S. Appl. No. 12/400,202, mailed Mar. 5, 2012.
Office Action for U.S. Appl. No. 12/400,202, mailed Aug. 8, 2012.
Office Action for Australian Application No. 2010326076, dated Jul. 8, 2013.
Notice of Reasons for Rejection for Japanese Application No. 2010-522104, mailed Feb. 12, 2013.
Office Action for U.S. Appl. No. 12/197,849, mailed Feb. 13, 2012.
Office Action for U.S. Appl. No. 12/197,849, mailed May 10, 2012.
Office Action for U.S. Appl. No. 12/197,849, mailed Sep. 17, 2012.
European Search Report for European Patent Application No. 10835039.8, mailed on Dec. 13, 2013, 8 pages.
Office Action for Japanese Application No. 2012-542152, mailed Mar. 14, 2014.

* cited by examiner

US 8,738,137 B2

SYSTEM FOR TRANSMITTING ELECTRICAL CURRENT TO A BODILY TISSUE

CROSS-REFERENCE TO RELATED APPLICATIONS

This application is a continuation-in-part of U.S. patent application Ser. No. 12/197,849, entitled "System for Transmitting Electrical Current to a Bodily Tissue," filed Aug. 25, 2008 now U.S. Pat. No. 8,467,880, which claims priority to U.S. Provisional Application Ser. No. 60/957,592, entitled "System for Transmitting Electrical Current to a Bodily Tissue," filed Aug. 23, 2007, each of which is incorporated herein by reference in its entirety.

BACKGROUND

The invention relates generally to medical devices, and specifically to a device for transmitting an electrical stimulation to a bodily tissue of a patient.

Known electrical stimulation systems are used in various medical procedures. For example, some known electrical stimulation systems are used to stimulate a response from a bodily organ or tissue of a patient, such as, for example, the heart, a muscle group or the like. Some known electrical stimulation systems are used to treat acute and/or chronic pain. One known electrical stimulation system, for example, is a transcutaneous electrical nerve stimulation (TENS) unit that provides an electrical stimulation to an electrode attached to the skin of the patient. The TENS unit includes a battery that must be sufficiently large to provide enough energy for a desired treatment period, often a period of several months, of electrical stimulation before replacement. Such a battery, however, may be obtrusive and/or burdensome for a patient to wear, for example, when the patient is in a long-term treatment program. The TENS unit is connected to the skin electrodes by wires extending from the unit to the electrodes. Exposure of such wires to moisture or fluid, for example as occurs during bathing, swimming, and/or perspiration, may result in unintended current loss or transfer, or shorting of the battery. The presence of such wires can also be cumbersome and/or aesthetically unappealing for the patient. Furthermore, the electrode can lose its electrical and/or mechanical properties within several days, so regular replacement of the electrode is required.

Some known systems are configured for use with a shorter-life battery; however, the system must be designed with a housing that can be opened to remove a used battery and to insert a new battery. Such a design can result in a bulky device that must be worn by the patient.

Some known systems necessitate several connections between an electrode patch and a stimulator. For example, known systems can include three or four connections between the patch and the stimulator. Each additional connection increases the risk that the battery and/or the electrical circuit can be shorted, for example due to the connectors being exposed to moisture, as described above.

What is needed is a compact medical device having a smaller battery configured to provide power for a greater duration or a duration similar to the length of time during which an electrode retains its electrical and/or mechanical properties on a body of a patient. A need also exists for a compact medical device that is configured to reduce the risk of a short circuit and/or leakage of an electrical current, such as by having a reduced number of mechanical connections with an external stimulator and/or by having water-resistant components. A need exists for a medical device capable of conforming to the curvature of a bodily tissue and providing structural integrity to support an electronic device. A need also exists for a medical device having a simplified manufacturing and/or assembly process.

SUMMARY OF THE INVENTION

In some embodiments, an apparatus includes a substantially rigid base and a flexible substrate. The substantially rigid base has a first protrusion and a second protrusion, and is configured to be coupled to an electronic device. The flexible substrate has a first surface and a second surface, and includes an electrical circuit configured to electronically couple the electronic device to at least one of an electrode a battery, or an antenna. The flexible substrate is coupled to the base such that a first portion of the second surface is in contact with the first protrusion. A second portion of the second surface is non-parallel to the first portion.

DETAILED DESCRIPTION

Figure 1:
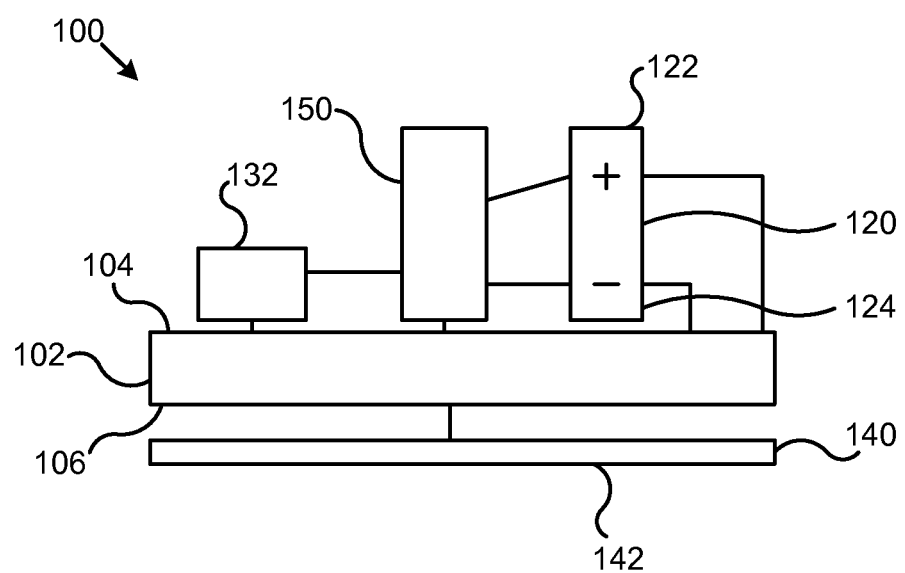
FIG. 1 is a schematic illustration of an apparatus according to an embodiment.

Apparatus and methods for transmitting an electrical signal (e.g., a current or stimulation) from an electronic device (e.g., an external stimulator) to a bodily tissue of a patient are described herein. Also described herein are methods for assembling a portion of a stimulator assembly for use in transmitting the electrical signal from the electronic device to the bodily tissue. In some embodiments, an apparatus is configured to be disposed on bodily tissue (e.g., skin) of a patient. The apparatus is configured to receive an electrical input from an external stimulator via a connector and to transmit the electrical input as an electrical current to an electrode disposed on or proximate to the bodily tissue. In this manner, the apparatus transmits the electrical stimulation to the bodily tissue.

As used herein, bodily tissue can include any tissue of a patient suitable for receiving and/or conveying an electrical stimulation. Bodily tissue can include, for example, nervous tissue, such as a nerve, the spinal cord, or another component of the peripheral or central nervous system. In another example, bodily tissue can include muscle tissue, such as, for example, skeletal muscle, smooth muscle, or cardiac muscle. Specifically, bodily tissue can include a group of tissues forming an organ, such as, for example, the skin, lungs, cochlea, heart, bladder, or kidney. In still another example, bodily tissue can include connective tissue, such as, for example, skin, bone or bone-like tissue.

The apparatus is configured to treat a variety of medical conditions, including acute and/or chronic pain, and/or to activate a motor point. For example, the apparatus can be configured to transmit an electrical current that at least partially activates conduction and/or propagation of action potentials (nerve impulses) along the axons of a target nerve associated with a target bodily tissue. In another example, the apparatus can be configured to transmit to the bodily tissue an electrical current that at least partially blocks the conduction and/or propagation of action potentials along the axons of the target nerve associated with the target bodily tissue.

The apparatus can be configured for transcutaneous and/or percutaneous stimulation of the target bodily tissue. In a treatment or procedure for transcutaneous stimulation, for example, the apparatus is configured to transmit an electrical stimulation through bodily tissue from a first electrode positioned on a first location of the patient's skin to a second electrode positioned on a second location on the patient's skin different from the first location. The pathway of the electrical current through the bodily tissue of the patient is a transcutaneous stimulation pathway. In a treatment or procedure for percutaneous stimulation, for example, the apparatus is configured to transmit an electrical stimulation to bodily tissue via an electrical lead. The electrical lead helps direct the electrical current to the target bodily tissue. In some procedures, the electrical lead can be completely implanted within the bodily tissue. In other procedures, the electrical lead is partially implanted within the bodily tissue such that a portion of the lead extends through the skin.

In some embodiments, the apparatus can be a portion of a system for stimulation of the target bodily tissue. For example, in some embodiments, the apparatus includes a substrate and a base, wherein the apparatus is configured for use with an electronic device to deliver an electrical current to the target bodily tissue. In another example, the apparatus includes a housing configured to be disposed about a portion of a stimulator assembly that is configured to transmit an electrical current to the target bodily tissue.

As used in this specification, the singular forms "a," "an" and "the" include plural referents unless the context clearly dictates otherwise. Thus, for example, the term "a material" is intended to mean one or more materials, or a combination thereof.

FIG. 1 is a schematic illustration of an apparatus 100 according to an embodiment. The apparatus 100 is configured to transmit an electrical current from a stimulator (not shown) through a bodily tissue of a patient. In this manner, the apparatus 100 is configured to stimulate a target bodily tissue. The apparatus 100 can be, for example, an electrode-battery assembly.

The apparatus 100 is configured to be disposed on or proximate to a patient's body, for example, on the skin of the patient. The apparatus 100 can be coupled to the skin of the patient with an adhesive, a bandage, or the like, or any combination of the foregoing.

The apparatus 100 includes a substrate 102, a power source 120, a connector 132, electrical circuitry 150, and an electrode assembly 140. The substrate 102 has a first surface 104 and a second surface 106 different than the first surface 104. The substrate 102 is configured to be disposed on or proximate to the body of the patient. When the apparatus 100 is disposed on the patient's body, the second surface 106 of the apparatus faces the patient's tissue, e.g., the skin.

The power source 120 is configured to provide power to an external stimulator (not shown) coupled to the apparatus 100. The power source 120 can be any suitable energy supplying source. For example, in some embodiments, the power source 120 is a battery. In some embodiments, the power source 120 is an ultracapacitor or a supercapacitor. The power source 120 is coupled to the substrate 102. In the schematic illustration, the power source 120 has a positive terminal 122 and a negative terminal 124. Each of the positive terminal 122 and the negative terminal 124 are coupled to the substrate 102.

The connector 132 is configured to electrically couple the external stimulator to the power source 120 and/or the electrical circuitry 150. The connector 132 can be any suitable mechanism for electrically coupling the external stimulator and the power source 120. For example, in some embodiments, the connector 132 is configured to provide both a mechanical and an electrical connection between the apparatus 100 and the external stimulator. Said another way, when the external stimulator is mechanically coupled to the apparatus 100 via the connector 132, the external stimulator is also placed in electrical communication with the power source 120. The connector 132 can be any suitable connector, including but not limited to, a snap-fit connector. In some embodiments, the connector 132 is a metal electrode. In some embodiments, the connector 132 is configured to provide a wireless electrical connection between the external stimulator and the power source 120. In some embodiments, for example, the connector is an antenna configured to transmit a signal to and/or receive a signal from the external stimulator. In some embodiments, the connector is a conductive ink, a wire, or the like.

The connector 132 is disposed proximate to the first surface 104 of the substrate 102. In some embodiments, for example, the connector is embedded in the first surface 104 of the substrate 102. In some embodiments, the connector 132 is disposed on top of the first surface 104 of the substrate 102. For example, the connector 132 can be a conductive ink printed onto the first surface 104 substrate. In still other embodiments, a portion of the connector 132 is embedded in the substrate and another portion of the connector extends from the first surface 104. As illustrated in FIG. 1, the connector 132 is electrically coupled to at least one of the positive terminal 122 and the negative terminal 124 of the power source 120.

The electrical circuitry 150 is coupled to the substrate 102. The electrical circuitry 150 is configured to electrically couple the connector 132 to the at least one of the positive terminal 122 and the negative terminal 124 of the power source 120. In some embodiments, for example, the electrical circuitry 150 includes a wire configured to electrically connect the connector to the power source 120. In some embodiments, a portion of the electrical circuitry 150 is a pathway of conductive ink printed onto the substrate 102.

At least one of the connector 132 or the electrical circuitry 150 is configured to prevent a short circuit of the electrical circuit contained therein. The electrical circuitry 150 can include a variety of suitable mechanisms configured to prevent shorting the electrical circuit (including shorting of the power source 120). For example, in some embodiments, the electrical circuitry 150 includes a fuse configured to open the electrical circuit in the presence of a threshold electrical load. In some embodiments, the electrical circuitry 150 includes a switch biased towards an open position such that the electrical circuit is incomplete until the switch is moved to a closed position. In some embodiments, the electrical circuitry 150 includes a diode configured to prevent flow of an electrical current in an undesired direction. In some embodiments, the connector 132 is configured as a wireless connector. For example, the connector 132 can be an antenna or a coil configured to wirelessly transmit and/or receive an electrical current between the external stimulator and the power source 120. In this manner, the connector 132 can be disposed below a surface of the apparatus 100 or otherwise covered such that the connector 132 is isolated from sources of moisture.

The electrode assembly 140 is coupled to the second surface 106 of the substrate 102. The electrode assembly 140 includes at least one electrode 142. The electrode 142 is configured to contact bodily tissue. For example, in some embodiments, the apparatus 100 includes a gel electrode 142 configured to adhere to the patient's skin. The electrode 142 is configured to facilitate transmission of an electrical current through the bodily tissue.

FIGS. 2-8 illustrate an apparatus 200 according to an embodiment. The apparatus 200 is configured to be disposed on a tissue (e.g., the skin) of a patient. The apparatus 200 includes a substrate 202, a power source 220, a connection assembly 230, electrical circuitry 250, and an electrode assembly 240.

The substrate 202 of the apparatus 200 is a printed circuit board ("PCB"). The PCB 202 has a first surface 204 (see, e.g., FIG. 2) and a second surface 206 (see, e.g., FIG. 4). In use, the second surface 206 of the PCB 202 faces the body of the patient and the first surface 204 faces away from the body of the patient. The PCB 202 is flexible such that the PCB can substantially conform to the contours of the portion of the patient's body on which the apparatus 200 is disposed. For example, the PCB 202 can be configured to be flexible such that the PCB conforms to the curvature of a patient's arm, leg, or back. In this manner, the PCB 202 is configured to facilitate positioning and placement of the apparatus 200 on the patient's body.

Figure 2:
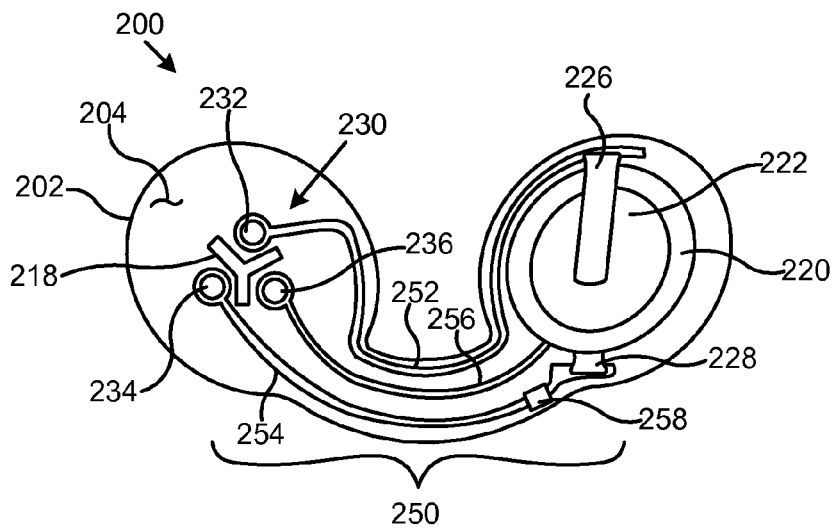
FIG. 2 is a top view of an apparatus according to an embodiment.
Figure 3A:
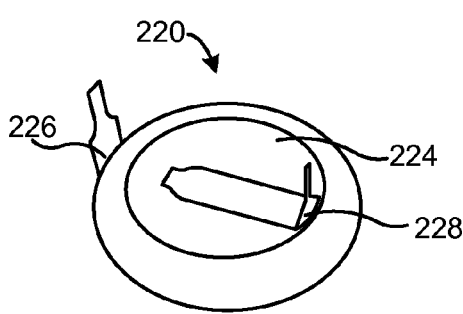
FIGS. 3A-3B are perspective views of a negative terminal and a positive terminal, respectively, of a portion of the apparatus of FIG. 2.
Figure 3B:
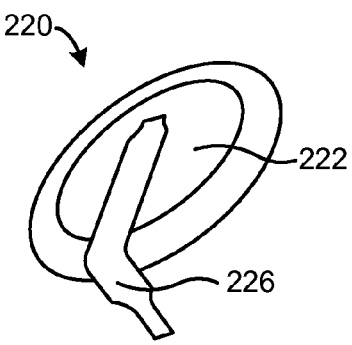

The power source 220 is configured to provide power to an external stimulator S (see, e.g., FIG. 6) coupled to the apparatus 200. The power source 220 is a battery coupled to the PCB 202. Specifically, the battery 220 is coupled to the PCB 202 by electrically conductive tabs 226, 228. As illustrated in FIGS. 2, 3A, and 3B, the battery has a positive terminal 222 and a negative terminal 224. A first electrically conductive tab 226 is coupled to the positive terminal 222. A second electrically conductive tab 228 is coupled to the negative terminal 224. Each of the first and second electrically conductive tabs 226, 228 are coupled to the PCB 202. The electrically conductive tabs 226, 228 can be coupled to the PCB by any suitable coupling mechanism. For example, each electrically conductive tab 226, 228 can be coupled to the PCB 202 by at least one of a solder joint, a braze joint, a weld, an adhesive, a mechanical coupler, or the like, or any combination of the foregoing. Each of the first and second electrically conductive tabs 226, 228 provides an electrical connection between its respective positive terminal 222 or negative terminal 224 of the battery 220 and the electrical circuitry 250, as described in more detail herein.

The connection assembly 230 includes a first connector 232, a second connector 234, and a third connector 236. The connectors 232, 234, 236 are disposed proximate to the first surface 204 of the PCB 202. The first and second connectors 232, 234, in conjunction with the electrical circuitry 250, are configured to electrically couple the battery 220 and the external stimulator S. Specifically, the first connector 232 is electrically coupled to the positive terminal 222 of the battery 220 via the electrical circuitry 250, and the second connector 234 is electrically coupled to the negative terminal 224 of the battery via the electrical circuitry.

The electrical circuitry 250 is at least partially coupled to the PCB 202. In some embodiments, at least a portion of the electrical circuitry 250 is a conductive material printed onto the PCB 202. As illustrated in FIG. 2, the electrical circuitry 250 includes a first electrical pathway 252, a second electrical pathway 254, and a third electrical pathway 256. The first electrical pathway 252 extends from the first connector 232 to the first electrically conductive tab 226, which is coupled to the positive terminal 222 of the battery 220. The first electrical pathway 252 is electrically coupled to the first electrically conductive tab 226, such as by at least one of a solder, a weld, a braze joint, a conductive adhesive, a mechanical coupler, or the like, or any combination of the foregoing. Thus, the electrical circuitry 250, via the first electrical pathway 252, electrically couples the first connector 232 to the positive terminal 222 of the battery 220.

The second electrical pathway 254 extends from the second connector 234 to the second electrically conductive tab 228, which is coupled to the negative terminal 224 of the battery 220. The second electrical pathway 254 is electrically coupled to the second electrically conductive tab, such as by at least one of a solder, weld, braze joint, a conductive adhesive, a mechanical coupler, or the like, or any combination of the foregoing. Thus, the electrical circuitry 250, via the second electrical pathway 254, electrically couples the second connector 234 to the negative terminal 224 of the battery 220. In this manner, when the external stimulator S is coupled to the apparatus 200 via the first and second connectors 232, 234, a power circuit is completed between the battery 220 and the external stimulator. When the power circuit is completed, the battery 220 can provide power to the external stimulator S, which the external stimulator can use to generate an electrical current for stimulating bodily tissue, as described in more detail herein.

The connection assembly 230 is configured to prevent a short circuit of the electrical circuit. The connection assembly 230 includes a hydrophobic barrier 218 coupled to the substrate 202. As illustrated in FIG. 2, the hydrophobic barrier is a Y-shaped barrier configured to increase impedance of the electrical current between the first connector 232, second connector 234, and/or the third connector 236, for example, when a portion of the substrate is wetted. An experiment testing the impedance of such a barrier is described below with reference to FIGS. 20-22. In use, the apparatus 200 may be wetted or otherwise exposed to a source of moisture, for example water or perspiration, which can create a leakage path for the electrical current between the first connector 232, the second connector 234, and/or the third connector 236 of the connection assembly 230. Such a leakage path for the electrical current can interfere with delivery of the electrical current intended to stimulate the bodily tissue and/or can cause leakage and discharge of the battery 220. The hydrophobic barrier 218 increases the impedance between at least one of the connectors 232, 234, 236 and another of the connectors 232, 234, 236 and/or the wet surface of the substrate 202. The hydrophobic barrier 218 can be constructed of any suitable material, including, but not limited to, plastic, rubber, glue, or another substantially non-conductive material.

The electrical circuitry 250 is also configured to prevent a short circuit of the electrical circuit. Specifically, as illustrated in FIG. 2, the electrical circuitry 250 includes a fuse 258 in the second electrical pathway 254. The fuse 258 is coupled to the PCB 202. For example, the fuse 258 can be at least partially embedded in the PCB 202.

The fuse 258 has a closed configuration and an open configuration. When the fuse 258 is in its closed configuration, the electrical circuitry 250 is configured to allow transfer of an electrical current through the circuitry between the battery 220 and the electrically coupled external stimulator S. In other words, the electrical circuit is closed or complete. When the fuse 258 is in an open configuration, a gap or interruption exists in the second electrical pathway 254. In other words, the electrical circuit is open or incomplete. The transfer of electrical current through the electrical circuitry 250 between the battery 220 and the external stimulator S is inhibited when the circuit is open. As such, the battery 220 is substantially inhibited from providing power to the external stimulator S when the fuse is in its open configuration.

The fuse 258 is configured to be in (or is moved to) its open configuration in the presence of a threshold electrical load. For example, the fuse 258 can be a metal wire or strip configured to melt under an abnormally high electrical load. In another example, the fuse 258 can be configured to break under a threshold electrical load. For example, during use on the body of a patient, the connectors 232, 234, 236 of the connection assembly 230 can be exposed when the external stimulator S is not mechanically coupled to the apparatus 200. The exposed connectors 232, 234, 236 create a risk of shorting the battery 220, for example by exposure to fluid or an electrical charge, which can cause heating and/or explosion of the battery. The fuse 258, however, is configured to open the electrical circuit in the presence of the threshold electrical load to prevent such a short of the battery.

The electrical circuitry 250 also forms a portion of a stimulation circuit. The stimulation circuit includes the third connector 236, a portion of the electrical circuitry 250, such as the third electrical pathway 256, and the electrode assembly 240. The stimulation circuit is complete when the external stimulator is coupled to the third connector 236. The electrical circuitry 250 of the stimulation circuit is configured to receive an electrical current from the external stimulator via the third connector 236. The electrical circuitry 250 is configured to transmit the electrical current to at least one of a first electrode 242 and a second electrode 244. The electrical circuitry 250 is also configured to receive at least a portion of the electrical current from at least one of the first electrode 242 and the second electrode 244. The electrical circuitry 250 transmits the received electrical current to at least one of the external stimulator S or the battery 220.

Figure 4:
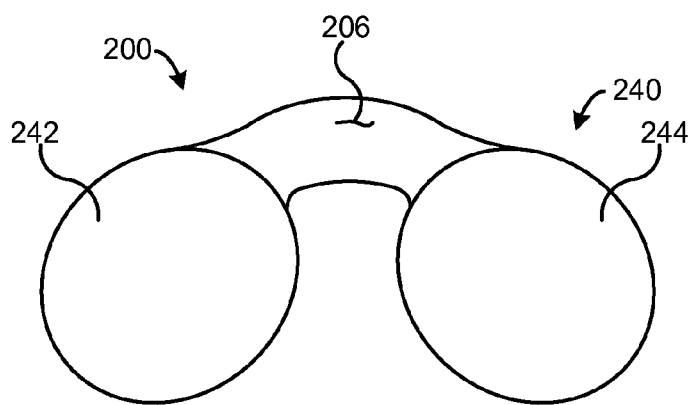
FIG. 4 is a bottom view of the apparatus of FIG. 2.
Figure 7:
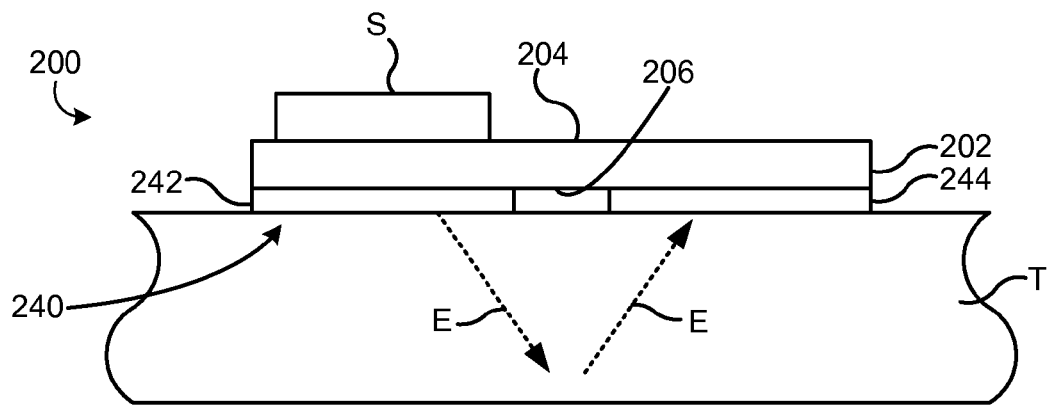
FIGS. 7-8 are side views of the apparatus of FIG. 2 coupled to an external stimulator and disposed on bodily tissue and delivering an electrical current to the bodily tissue and to an implanted conductive lead, respectively.
Figure 8:
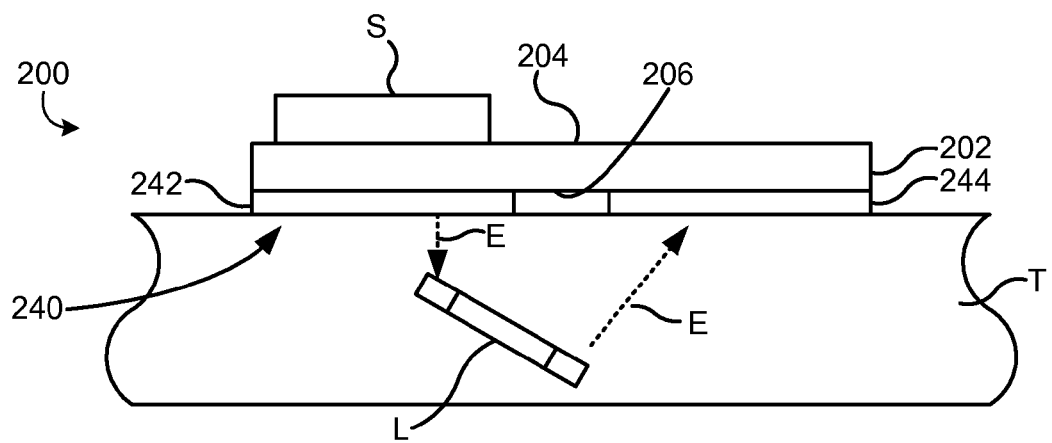

The electrode assembly 240 of the apparatus 200 is coupled to the second surface 206 of the PCB 202, as illustrated in FIG. 4. The electrode assembly 240 includes the first electrode 242 and the second electrode 244. As illustrated in FIGS. 7-8, each of the first electrode 242 and the second electrode 244 is configured to contact bodily tissue T and to facilitate transmission of an electrical current E through the bodily tissue, for example through subcutaneous bodily tissue located below and/or between the first electrode 242 and the second electrode 244. The first electrode 242 is configured to facilitate transmission of the electrical current E from the external stimulator S through the bodily tissue T. The first electrode 242 can facilitate transmission of the electrical current E to an electrical lead L at least partially implanted within the bodily tissue, as illustrated in FIG. 8. The second electrode 244 is configured to receive at least a portion of the electrical current E. As illustrated in FIGS. 7-8, for example, the second electrode 244 can receive electrical current E that has passed through the bodily tissue T and/or through an electrical lead L at least partially implanted within the bodily tissue. The transmission of current to an implanted lead is described, for example, in U.S. patent application Ser. No. 11/337,824, which is incorporated herein by reference in its entirety.

The electrodes 242, 244 are configured to adhere to bodily tissue (e.g., the skin) of the patient. Each electrode 242, 244 of the electrode assembly 240 includes a gel on the tissue-facing surface of the electrode. The gel can be any suitable known gel including, but not limited to, wet gels, karaya-gum-based hydrogels, and/or synthetic copolymer-based hydrogels. The first electrode 242 and second electrode 244 can be, for example, a cathodic gel electrode and an anodic gel electrode, respectively.

Figure 5:
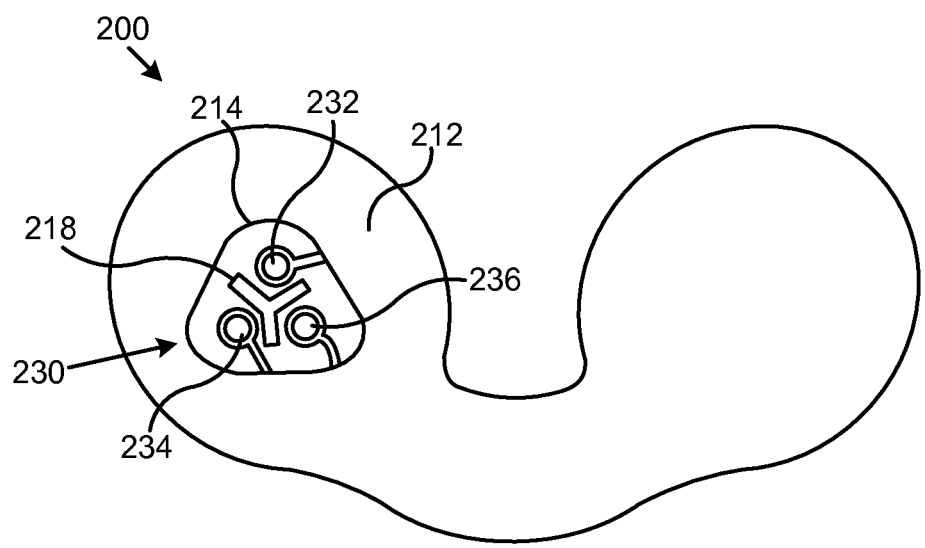
FIG. 5 is a top view of the apparatus of FIG. 2 with a portion of the apparatus in a covering.
Figure 6:
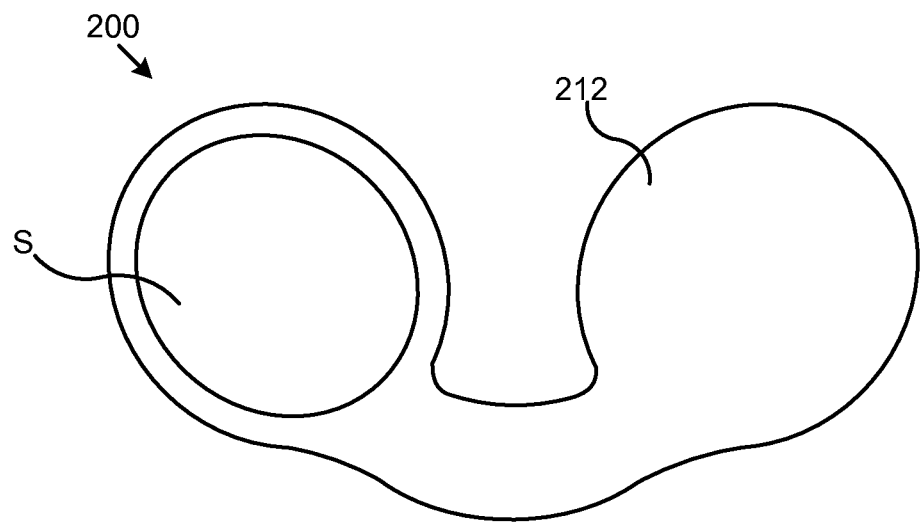
FIG. 6 is a top view of the apparatus of FIG. 5 coupled to an external stimulator.

As illustrated in FIG. 5, the apparatus 200 can be at least partially enclosed by a material 212, such as a material configured to increase the comfort of the patient utilizing the apparatus and/or protect components of the apparatus from external elements. The material at least partially encloses at least one of the first surface 204 of the PCB 202, the battery 220, and a portion of the electrical circuitry 250. The material 212 defines an opening 214 through which the connection assembly 230 is accessible. In this manner, the external stimulator S can be physically coupled to the apparatus 200 via the connection assembly 230, as illustrated in FIG. 6. The material 212 can be any suitable material including, for example, a foam, a water-proof material, plastic, an insulative material, a non-conductive material, a film, or the like, or any combination of the foregoing.

In use, a target bodily tissue is identified as the target for electrical stimulation. The apparatus 200 is positioned proximate to the identified target bodily tissue, such as on a surface of the patient's skin proximate to a subcutaneous target bodily tissue. For example, the apparatus 200 can be positioned proximate to an arm, leg, back, or other portion of the patient's body. The first and second electrodes 242, 244 are adhered to the patient's skin in the desired position.

The external stimulator S is placed in electrical communication with the battery 220 of the apparatus 200. The external stimulator S is electrically coupled to the battery 220 by coupling the external stimulator to the connectors 232, 234. The battery 220 provides power to the external stimulator S. In response to receiving power from the battery 220, the external stimulator S generates an electrical current and transmits the electrical current to the apparatus 200 via at least one connector 232, 234, 236. The electrical current is transmitted via the electrical circuitry 250 to the first electrode 242. The first electrode 242 transmits at least a portion of the electrical current E through the bodily tissue of the patient, as illustrated in FIG. 7. In some embodiments, as illustrated in FIG. 8, a portion of the electrical current E transmitted from the first electrode 242 through the bodily tissue is picked by a proximal end portion of an electrical conductor L (or lead) at least partially implanted within the bodily tissue, as illustrated in FIG. 8. The electrical conductor L is configured to transmit a portion of the electrical current E from its proximal end portion to a distal end portion of the electrical conductor L. The electrical current E is transmitted from the distal end portion of the electrical conductor L through the bodily tissue T to the second electrode 244. At least a portion of the electrical current E is received by the second electrode 244. The electrical circuitry 250 transmits the electrical current E to at least one of the battery 220 or the external stimulator S to complete one cycle of electrical stimulation of the target bodily tissue. The cycle of electrical stimulation of the target bodily tissue is repeated as necessary. The apparatus 200 is disposable and can be removed from the patient and discarded when it is no longer needed or suitable for treatment, such as, for example, when a prescribed course of treatment is completed or when the battery is exhausted.

Although the substrate 202 has been illustrated and described as being a PCB, in other embodiments, the substrate can be constructed of a different material. For example, the substrate can be constructed of silicon, polyamide, or another suitable polymer, or any combination of the foregoing.

Furthermore, although at least a portion of the electrical circuitry 250 and/or the connection assembly 230 has been illustrated and described as being a conductive ink printed on a surface of the substrate 202, in other embodiments, at least one of the electrical circuitry and the connection assembly can be differently constructed. For example, the connection assembly can include a connector that is a wire, an antenna, a metal electrode, or the like. In another example, at least a portion of electrical circuitry can include or be a wire or another electrically conductive material.

Although the material 212 is illustrated as at least partially enclosing at least one of the first surface 204 of the PCB 202, the battery 220, and a portion of the electrical circuitry 250, in other embodiments, a material can be disposed over a different portion of the apparatus 200. For example, in some embodiments, the material can be an insulative film disposed over a portion of the electrical circuitry.

Although the apparatus 200 has been illustrated and described as being adhered to the body of the patient via adhesive gel electrodes, in other embodiments, an apparatus can be coupled to the patient with a tape, a strap, a band, a glue, or another adhesive, or any combination of the foregoing. Furthermore, an apparatus that includes a glue, another adhesive, or the like, to adhere to the patient can include the glue, other adhesive, or the like on all or a portion of the portion of the apparatus contacting the body of the patient.

Figure 9A:
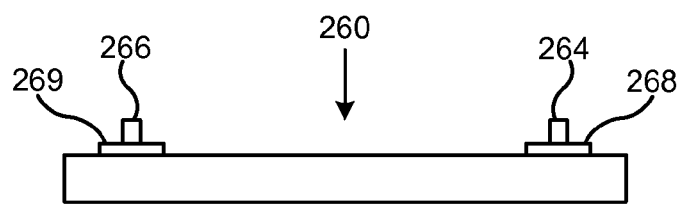
FIGS. 9A-9C are side views of portions of apparatus according to embodiments.
Figure 9B:
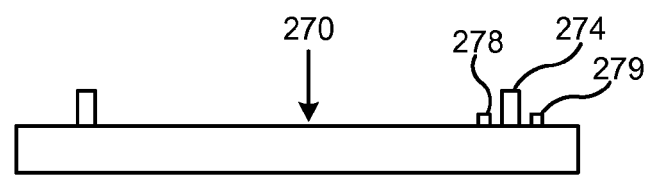
Figure 9C:
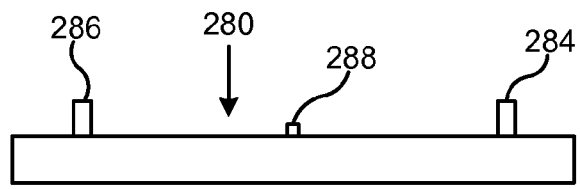

Although the apparatus 200 has been illustrated and described as having a connection assembly 230 including a Y-shaped hydrophobic barrier 218, in other embodiments, an apparatus can include a barrier having a different configuration. For example, as illustrated in FIG. 9A, in some embodiments, an apparatus 260 can include a barrier 268, 269 disposed about at least a portion of at least one connector 264, 266. In another example, in some embodiments, as illustrated in FIG. 9B, an apparatus 270 can include a plurality of barriers 278, 279 positioned at least on opposing sides of at least one connector 274. In still another example, as illustrated in FIG. 9C, in some embodiments, an apparatus can include a non-Y-shaped barrier 288 positioned between at least a first connector 284 and a second connector 286.

Figure 10:
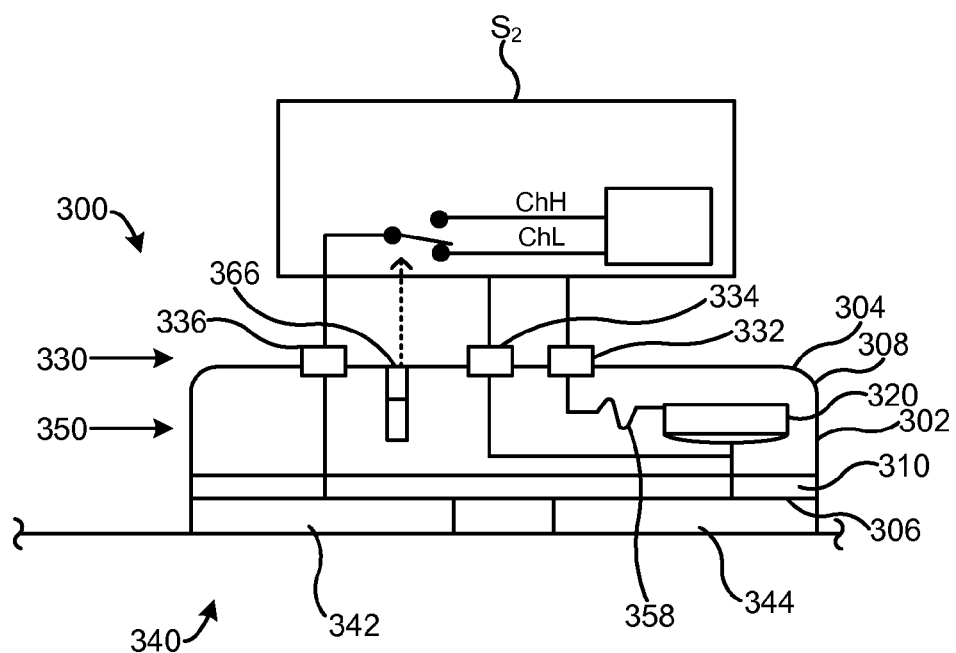
FIGS. 10-14 are side views of an apparatus according to embodiments and an external stimulator.

FIG. 10 is an illustration of an apparatus 300 according to an embodiment. The apparatus 300 is configured to transmit an electrical current from an external stimulator $S_2$ to a target bodily tissue. The apparatus includes a substrate 302, a power source 320, a connection assembly 330 including three connectors 332, 334, 336, electrical circuitry 350 including a fuse 358, and an electrode assembly 340.

The substrate 302 includes a first layer 308 having a first surface 304 and a second layer 310 having a second surface 306 different than the first surface. As illustrated in FIG. 10, each of the power source 320, the connectors 332, 334, 336, and the electrical circuitry 350 is at least partially embedded in the first layer 308 of the substrate 302. The first layer 308 of the substrate is formed of a first material. The second layer 310 of the substrate is formed over a portion of the electrode assembly 350. The second layer 310 of the substrate is formed of a second material different than the first material.

As illustrated in FIG. 10, the apparatus 300 includes a magnet 366 coupled to the substrate 302. The magnet 366 is configured to move a switch in the external stimulator from a first position in which the switch is electrically coupled to a first output channel to a second position in which the switch is electrically coupled to a second output channel different than the first output channel. For example, as illustrated in FIG. 10, movement of the magnet 366 from its first position can move the switch from a first position in which the switch is coupled to a high output channel (indicated as ChH) to a second position in which the switch is coupled to a low output channel (indicated as ChL). In this manner, the magnet 366 can be used to control an amount of electrical current output from the external stimulator $S_2$ to the apparatus 300.

Figure 11:
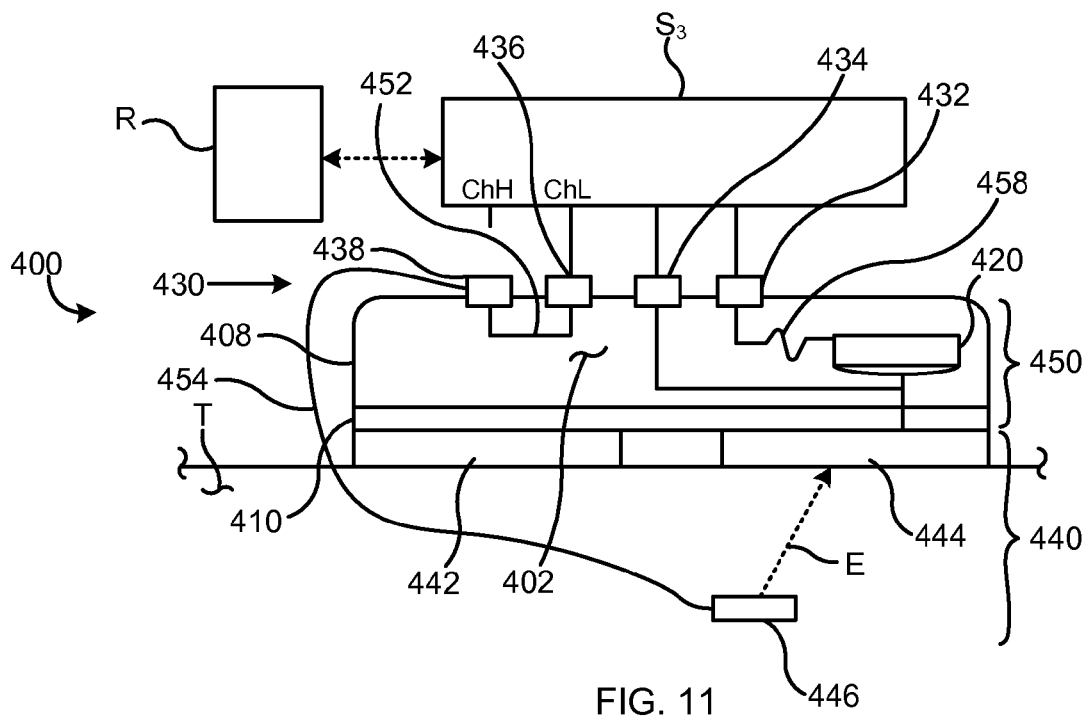

Although the apparatus 200, 300 have been illustrated and described as including at first electrode 242, 342 and a second electrode 244, 344 disposed on a second surface 206, 306 of a substrate 202, 302 and configured to facilitate transmission of an electrical current from an external stimulator S, $S_2$ through the bodily tissue, in some embodiments, an apparatus is configured to deliver or transmit the electrical current to the bodily tissue in a different manner. For example, as illustrated in FIG. 11, an apparatus 400 according to an embodiment is an electrode-battery assembly configured for percutaneous delivery of an electrical current to target bodily tissue.

The electrode-battery assembly 400 includes a substrate 402, a battery 420, a connection assembly 430, electrical circuitry 450, and an electrode assembly 440. The substrate 402 has a first layer 408 and a second layer 410. The battery 420, and electrical circuitry 450 are at least partially embedded in the first layer 408 of the substrate. The electrical circuitry 450 includes a fuse 458 configured to open the electrical circuit in the presence of a threshold electrical load, as described above.

An external stimulator $S_3$ is electrically coupled to the electrode-battery assembly 400 via the connection assembly 430. The connection assembly 430 includes a first connector 432, a second connector 434, a third connector 436, and a fourth connector 438. The connectors 432, 434, 436, 438 of the connection assembly 430 extend from a surface of the first layer 408 of the substrate 402.

The third connector 436 is configured to receive an electrical current input from the external stimulator $S_3$. The third connector 436 is configured to transmit the electrical current via a first electrical pathway 452 of the electrical circuitry 450 to the fourth connector 438. The fourth connector 438 is physically and electrically coupled to an electrode 446 of the electrode assembly 440 via a second electrical pathway 454. For example, as illustrated in FIG. 11, the fourth connector 438 is coupled to the second electrical pathway 454 including an electrical conductor exterior to the substrate 402 and extending from the fourth connector 438 to the electrode 446 implanted within the bodily tissue T.

The electrode assembly 440 includes a first electrode 442, a second electrode 444, and a third electrode 446. The first electrode 442 and second electrode 444 are coupled to the second layer 410 of the substrate 402. The third electrode 446 is coupled to the substrate 402 via the second electrical pathway 454 and is configured to be at least partially implanted within the bodily tissue T. At least the third electrode 446 is configured to transmit an electrical current from the external stimulator $S_3$ to the bodily tissue T. In use, the external stimulator $S_3$ transmits an electrical current to the third connector 436. The electrical current is transmitted from the third connector 436 via the first electrical pathway 452 to the fourth connector 438, and from the fourth connector via the second electrical pathway 454 to the third electrode 446. The third electrode 446 transmits at least a portion of the electrical current E to the bodily tissue, as illustrated in FIG. 11. The second electrode 444 is configured to receive at least a portion of the electrical current from the bodily tissue.

The electrode-battery assembly 400 is configured to receive an electrical current from the external stimulator $S_3$ via at least one of a first output channel and a second output channel of the external stimulator. For example, as illustrated in FIG. 11, the external stimulator $S_3$ has a high output channel ChH and a low output channel ChL. The electrode-battery assembly 400 is illustrated in FIG. 11 as being electrically coupled to the low output channel ChL of the external stimulator $S_3$ via the third connector 436, however, in use, a patient or practitioner operating the stimulator can selectively electrically couple the electrode-battery assembly to the high output channel ChH via the third connector.

The external stimulator $S_3$ can be wirelessly controlled by the operator. For example, the operator can wirelessly control the external stimulator $S_3$ using a remote control R to communicate with the stimulator over a radio frequency. In this manner, the operator can wirelessly program the external stimulator $S_3$, power on and/or off the external stimulator $S_3$, and/or select the desired output channel (e.g., ChH and/or ChL). In some embodiments, for example, the remote control R can a dedicated programming device for use specifically with the stimulation system. In other embodiments, however, the remote control R can be a personal digital assistant (PDA) or other hand-held computing device that is configured to communicate with the external stimulator $S_3$. Such a PDA or hand-held computing device can include, for example, a Central Processing Unit (CPU) and electronic memory, and can be generally used for storing and organizing information and for providing tools for everyday tasks. In such embodiments, the system can include an adaptor and/or cradle (not shown) configured to be coupled to and/or receive the PDA. The adaptor and/or cradle can enable the PDA to communicate with the external stimulator $S_3$ such that external stimulator $S_3$ can be wirelessly controlled by the operator, patient or other user. Although described as including an adaptor and/or cradle, in other embodiments, the external stimulator $S_3$ can be wirelessly controlled using a PDA and/or hand-held computing device without the need for an adaptor and/or cradle.

Although the apparatus 400 is illustrated and described as percutaneously transmitting the electrical current, in some embodiments, an apparatus is configured for both transcutaneous and percutaneous transmission of the electrical current. For example, an apparatus can be configured to transcutaneously transmit the electrical current through bodily tissue from a first electrode disposed on a surface of the patient's skin and percutaneously transmit the electrical current via a second electrode (e.g., similar to electrode 446 described above) at least partially implanted in the bodily tissue. In some embodiments, the high output channel ChH of the external stimulator is configured for transcutaneous stimulation and the low output channel ChL is configured for percutaneous stimulation of the target bodily tissue. Electrical current from each of the first electrode and the second electrode can be received by a third electrode disposed on the skin of the patient, similar to electrode 444 described above.

Figure 12:
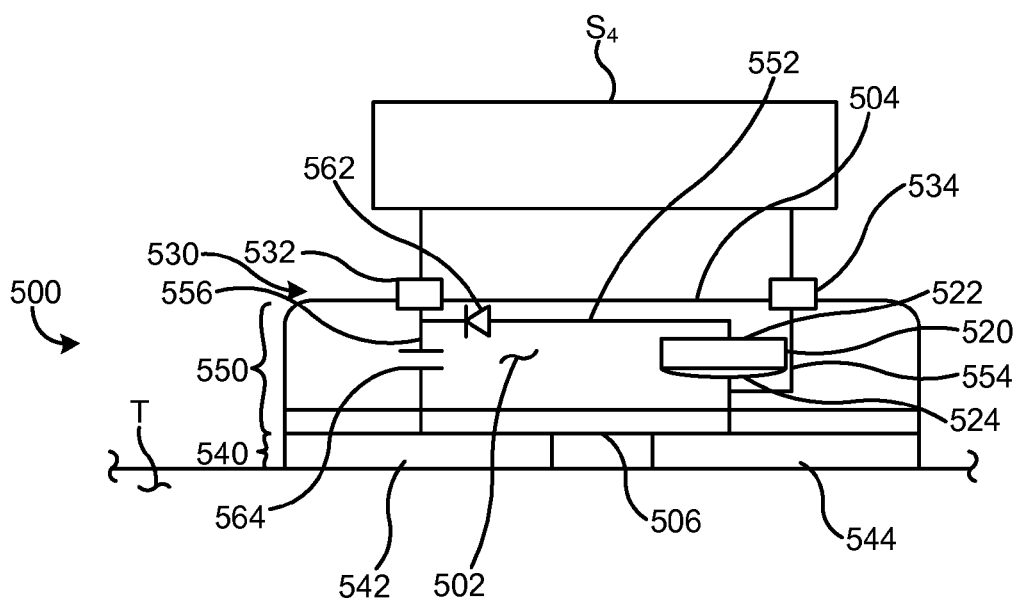

Although the apparatus 200, 300, 400 described above have been illustrated and described as including a fuse 258, 358, 458 configured to open the electrical circuit, in other embodiments, an apparatus 500 includes electrical circuitry differently configured to prevent a short circuit of the electrical circuit, as illustrated in FIG. 12. The apparatus 500 is configured to transmit an electrical stimulation to a bodily tissue and includes a substrate 502, an electrode assembly 540, a power source 520, and a connection assembly 530.

The substrate 502 has a first surface 504 and a second surface 506 different than the first surface. The power source 520 is coupled to the substrate 502 and can be any suitable source of power described herein. The power source 520 has a positive terminal 522 and a negative terminal 524. The power source 520 is configured to provide power to an external stimulator $S_4$, for example, when the external stimulator is in electrical communication with the power source.

The electrode assembly 540 is coupled to the second surface 506 of the substrate 502. The electrode assembly 540 is configured to facilitate transmission of an electrical current from the external stimulator $S_4$ through the bodily tissue. The electrode assembly includes a first electrode 542 and a second electrode 544 different than the first electrode.

The connection assembly 530 is coupled to the substrate 502 and includes up to two connectors configured to be in electrical communication with the external stimulator $S_4$. Specifically, as illustrated in FIG. 12, the connection assembly 530 includes a first connector 532 and a second connector 534. Each of the first connector 532 and a second connector 534 is coupled to the first surface 504 of the substrate 502. The first connector 532 is configured to electrically couple the external stimulator $S_4$ to the positive terminal 522 of the power source 520 and to the first electrode 542. The second connector 534 is configured to electrically couple the external stimulator $S_4$ to the negative terminal 524 of the power source 520 and to the second electrode 544.

The connection assembly 530 has a first configuration in which the two connectors 532, 534 are electrically coupled to the external stimulator $S_4$ (as illustrated in FIG. 12) and a second configuration in which the two connectors are electrically isolated from the external stimulator (not shown). When the connection assembly 530 is in its first configuration, the connection assembly completes a power circuit between the power source 520 and the external stimulator $S_4$ and a stimulation circuit between the external stimulator and the electrode assembly 540, as described in more detail herein.

The power circuit includes electrical circuitry 550, a diode 562, the connection assembly 530, and the power source 520. As illustrated in FIG. 12, the electrical circuitry 550 includes a first electrical pathway 552 and a second electrical pathway 554, each coupled to the substrate 502. The first electrical pathway 552 electrically couples the first connector 532 to the positive terminal 522 of the power source 520. The second electrical pathway 554 electrically couples the second connector 534 to the negative terminal 524 of the power source 520. When the connection assembly 530 is in its second configuration, the power circuit is open (or incomplete). When the connection assembly 530 is in its first configuration such that the first and second connectors 532, 534, respectively, are electrically coupled to the external stimulator $S_4$, the power circuit is closed (or complete) and the power source 520 provides power to the external stimulator.

The diode 562 is coupled to the substrate 502 and is disposed within the first electrical pathway 552. The diode 562 is configured to allow electrical current to flow in a first direction and to substantially inhibit flow of the electrical current in a second direction different than the first direction. As illustrated in FIG. 12, the diode 562 is configured to allow flow of the electrical current from the power source in a first direction towards the first electrode 542 via the first electrical pathway 552. The diode 562 is configured to substantially inhibit flow of the electrical current in a second direction opposite the first direction, such as from the first connector 532 to the power source 520 and/or to the second electrode 544 via the first electrical pathway 552. In this manner, the diode 562 is configured to prevent a short circuit of the electrical circuit because the stimulating electrical current transmitted from the external stimulator $S_4$ to the first connector 532 is substantially inhibited from flowing to the power source 520, which otherwise may cause the power source to overheat, explode, or otherwise become defective.

The stimulation circuit includes electrical circuitry 550, a capacitor 564, the connection assembly 530, and the electrode assembly 540. As illustrated in FIG. 12, the electrical circuitry 550 includes a third electrical pathway 556 coupled to the substrate 502. The third electrical pathway 556 electrically couples the first connector 532 to the first electrode 542 of the electrode assembly 540. The second electrical pathway 554 electrically couples the second connector 534 to the second electrode 544. As such, the negative terminal 524 of the power source 520 is also coupled to the second electrode 544.

The capacitor 564 is coupled to the substrate 502 and is disposed in the electrical circuitry 550, for example, in the third electrical pathway 556 as illustrated in FIG. 12. The capacitor 564 is configured to separate an alternating current from a direct current. The capacitor 564 is configured to substantially inhibit flow of the direct current from the power source 520 to the first electrode 542. The capacitor 564 is configured to deliver at least one of the alternating current and the direct current from the external stimulator to the first electrode.

When the connection assembly 530 is in its first configuration (and the power circuit is closed, as described above), the stimulation circuit is also closed and an electrical current can be transmitted from the external stimulator through the target bodily tissue via the apparatus 500. Specifically, the electrical current is transmitted from the external stimulator $S_4$ to the first connector 532. The first connector 532 transmits the electrical current towards the first electrode 542 via the third electrical pathway 556. The capacitor 564 separates direct current from alternating current, and then transmits at least one of the direct current or the alternating current to the first electrode 542. The first electrode 542 transmits the electrical current through the bodily tissue T. The second electrode 544 receives at least a portion of the electrical current from the bodily tissue T and transmits the electrical current to the electrical circuitry 550 of the apparatus 500.

Although the diode 562 has been illustrated and described as being configured to allow flow of the electrical current from the power source 520 in a first direction towards the first electrode 542 and to substantially inhibit flow of the electrical current in a second direction opposite the first direction, such as from the first connector 532 to the power source 520 and/or to the second electrode 544 via the first electrical pathway 552, in some embodiments, the diode 562 is configured to allow flow of the electrical current in the second direction and to substantially inhibit flow of the electrical current in the first direction.

Figure 13:
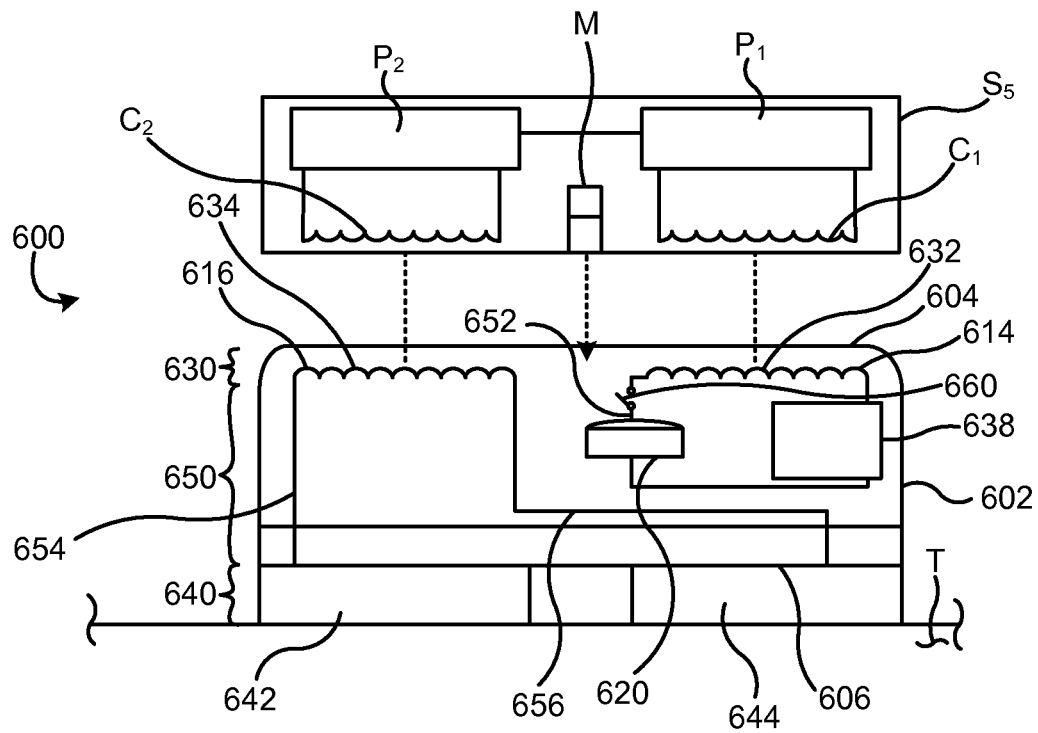

Although the apparatus 500 has been illustrated and described as being electrically coupled to the external stimulator via the two mechanical connectors 532, 534, in some embodiments, an apparatus is electrically coupled to the external stimulator in a different manner. For example, as illustrated in FIG. 13, in some embodiments, an apparatus 600 is wirelessly electrically coupled to an external stimulator $S_5$.

The apparatus 600 includes a substrate 602 configured to be positioned on or proximate to the bodily tissue T. The substrate 602 has a first surface 604 and a second surface 606 different than the first surface. The second surface 606 of the substrate is configured to face the bodily tissue and the first surface 604 is configured to face away from the bodily tissue when the apparatus is positioned on or proximate to the bodily tissue. A power source 620 is coupled to the substrate 602. As illustrated in FIG. 13, the power source 620 is at least partially embedded in the substrate 602.

The apparatus 600 includes a connection assembly 630 configured to be in electrical communication with an external stimulator $S_5$. The connection assembly 630 includes a first connector 632 and a second connector 634. Each of the first connector 632 and the second connector 634 is an antenna configured as a first coil 614 and a second coil 616, respectively, that is configured to be in wireless electrical communication with the external stimulator $S_5$. The first coil 614 and second coil 616 are each coupled to the first surface 604 of the substrate 602. Specifically, the coils 614, 616 are embedded in the substrate 602. In this manner, the coils 614, 616 are configured to prevent a short circuit of the electrical circuit, for example, by substantially preventing exposure of the coils to a fluid.

The connection assembly 630 has a first configuration in which the coils 614, 616 are electrically coupled to the external stimulator $S_5$ and a second configuration in which the coils are electrically isolated from the external stimulator. The connection assembly 630 is configured to complete a power circuit between the power source 620 and the external stimulator $S_5$ and a stimulation circuit between the external stimulator and an electrode assembly 640, as described in more detail herein.

As illustrated in FIG. 13, the power circuit includes the first coil 614, the power source 620, an oscillator 638, and electrical circuitry 650. The electrical circuitry 650 includes a switch 660 disposed in a first electrical pathway 652. The switch 660 can be any suitable switch for opening and closing a circuit. For example, the switch 660 can be a reed switch including a pair of contacts on ferrous metal reeds in a hermetically sealed glass envelope (not shown). The switch 660 has an open configuration (see, e.g., FIG. 13) and a closed configuration. In its open configuration, the pair of contacts of the reeds is open (or separate). Thus, the electrical circuit is open when the switch is in its open configuration. The switch 660 is movable to its closed configuration by the introduction of a magnetic field, such as by placing a magnet M in the external stimulator $S_5$ proximate to the switch. Specifically, the presence of the magnetic field causes the pair of contacts to close or otherwise come together. As such, the switch 660 is configured to close the electrical circuit when the switch is moved to its closed configuration. The switch 660 is biased to its open configuration. In this manner, the electrical circuitry is configured to prevent a short circuit of the electrical circuit.

The power source 620 is configured to transmit an electrical current to the electrical circuitry 650 when the connection assembly 630 is in its first configuration and the switch 660 is in its closed configuration. The electrical circuitry 650 is configured to transmit the electrical current to the oscillator 638. The oscillator 638 is configured to deliver at least one oscillation (of electrical current) to the first coil 614 to initiate wireless transmission of an electrical output from the first coil to the external stimulator $S_5$. The first coil 614 is configured to wirelessly transmit the electrical output to the external stimulator $S_5$, such as to a coil $C_1$. The coil $C_1$ of the external stimulator $S_5$ can transmit the electrical current to a source of power $P_1$ disposed within the external stimulator. The source of power $P_1$ can transmit the electrical current to a stimulation circuit and/or a radio frequency circuit coupled to the external stimulator $S_5$. For example, the source of power $P_1$ can transmit the electrical current to a portion of the stimulation circuit $P_2$ disposed on the external stimulator $S_5$.

As illustrated in FIG. 13, the stimulation circuit includes the second coil 616, electrical circuitry 650, and an electrode assembly 640. The second coil 616 is disposed proximate to the first surface 604 of the substrate 602. Specifically, the second coil 616 is embedded in the substrate 602 proximate the first surface 604. The second coil 616 is configured for wireless electrical communication between an electrode of the electrode assembly 640 and the external stimulator $S_5$. For example, the second coil 616 is configured to receive an electrical input from a coil $C_2$ of the external stimulator $S_5$ and to transmit at least a portion of the electrical input (or current) to the electrical circuitry 650.

The electrical circuitry 650 is configured to transmit the electrical current to the electrode assembly, for example, via a second electrical pathway 654. The electrode assembly 640 is coupled to the second surface 606 of the substrate 602 and includes a first electrode 642 and a second electrode 644 different than the first electrode. The first electrode 642 is coupled to the second electrical pathway 654 of the electrical circuitry 650. The first electrode 642 can receive an electrical current from the electrical circuitry 650 via the second electrical pathway 654 and can facilitate transmission of the electrical current through the bodily tissue. The second electrode 644 is configured to receive a portion of the electrical current from the bodily tissue. The second electrode 644 is configured to transmit the electrical current to the electrical circuitry 650, such as to a third electrical pathway 656. The electrical circuitry 650 can transmit the electrical current to the second coil 616. The second coil 616 can wirelessly transmit an electrical output to the external stimulator $S_5$.

Although the apparatus 600 is illustrated and described as being in wireless communication with the external stimulator $S_5$ via a connection assembly 630 including the first and second coils 614, 616, respectively, in some embodiments, an apparatus is in wireless communication with an external stimulator via a connection assembly having a different configuration. For example, in some embodiments, an apparatus includes at least one antenna configured to wirelessly communicate with an external stimulator.

Figure 14:
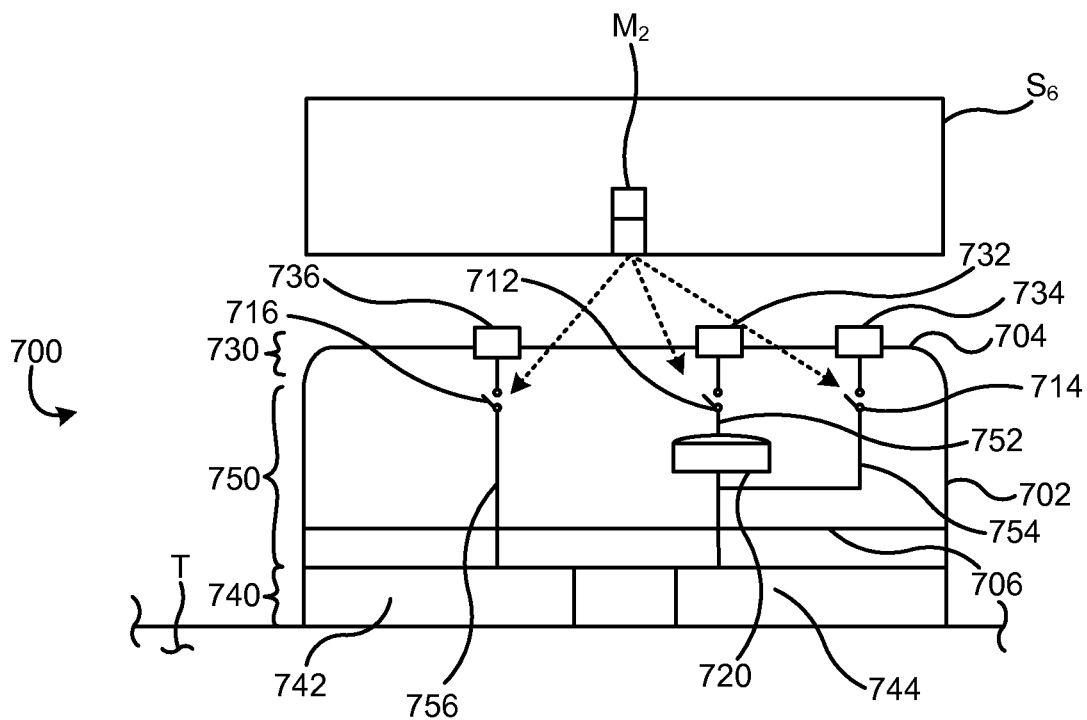

As illustrated in FIG. 14, an apparatus 700 includes a connection assembly 730 having a plurality of connectors that includes a first connector 732, a second connector 734, and a third connector 736. The connection assembly 730 is disposed proximate to a first surface 704 of a substrate 702. Each of the first connector 732, second connector 734, and third connector 736 is configured to be coupled to a counterpart connector (not shown) on the stimulator $S_6$. The first connector 732 is configured to be in electrical communication with a battery 720 coupled to the substrate 702 via a first electrical pathway 752 of electrical circuitry 750. The first electrical pathway 752 includes a first switch 712. The second connector 734 is configured to be in electrical communication with the battery 720 via a second electrical pathway 754. The second connector 734 is also configured to be in electrical communication with a first electrode 744 of an electrode assembly 740 coupled to the substrate 702 via the second electrical pathway 754. The electrode assembly 740 can be coupled, for example, to a second surface 706 of the substrate 702. The second electrical pathway 754 includes a second switch 714. The third connector 736 is configured to be in electrical communication with a second electrode 742 of the electrode assembly 740 via a third electrical pathway 756. The third electrical pathway 756 includes a third switch 716. Each switch 712, 714, 716 is configured to move from an open configuration to a closed configuration in the presence of a magnetic field. For example, as illustrated in FIG. 14, each switch 712, 714, 716 is configured to move to its respective closed configuration by a magnet $M_2$ coupled to the external stimulator $S_6$. When the switches 712, 714, 716 are each in the closed configuration, and the external stimulator $S_6$ is in electrical communication with the connection assembly 730, the electrical circuit is complete (or closed).

When the electrical circuit is complete, the battery 720 is configured to provide power to the external stimulator $S_6$. Power from the battery 720 enables the external stimulator to generate an electrical output to be received as an electrical input by the third connector 736. The second electrode 742 is configured to receive the electrical current from the third connector 736 via the third electrical pathway 756. The second electrode 742 is configured to transmit the electrical current through target bodily tissue T. The first electrode 744 is configured to receive at least a portion of the electrical current from the bodily tissue T and to transmit the electrical current to the external stimulator $S_6$ via the second electrical pathway 754.

Although the apparatus 600, 700 have been illustrated and described as including two antenna coils 614, 616 and three connectors 732, 734, 736, respectively, in other embodiments an apparatus can include any suitable combination of connectors, e.g., wired and/or wireless, for electrical communication with an external stimulator.

Figure 15:
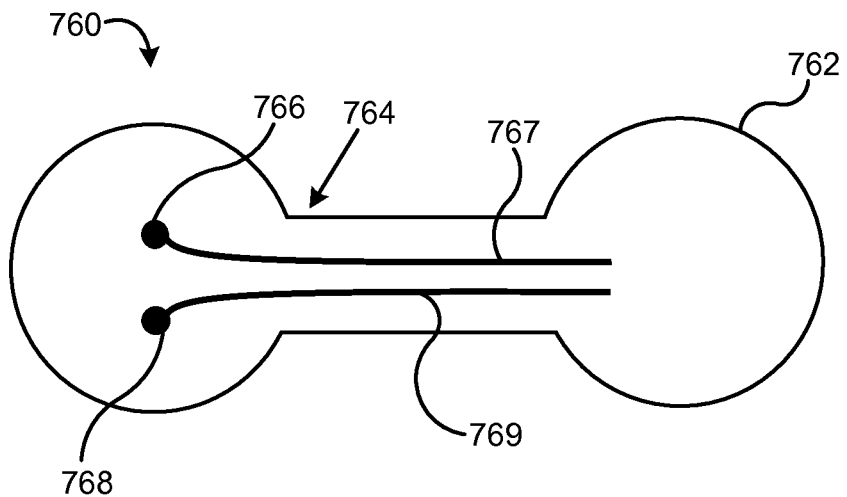
FIGS. 15-18 are top views of an antenna of an apparatus according to embodiments.

In some embodiments, as illustrated in FIG. 15, an apparatus 760 includes a planar dipole antenna 764 that is printed onto a substrate 762, such as a PCB. The antenna 764 includes a first connector 766, a first branch 767, a second connector 768, and a second branch 769. The first connector 766 is configured to be in electrical communication with an external stimulator (not shown). The first branch 767 is configured to electrically couple the first connector 766 to electrical circuitry (not shown) coupled to the substrate 762. The second connector 768 is configured to be in electrical communication with the external stimulator. The second branch 769 is configured to electrically couple the second connector 768 to the electrical circuitry.

Figure 16:
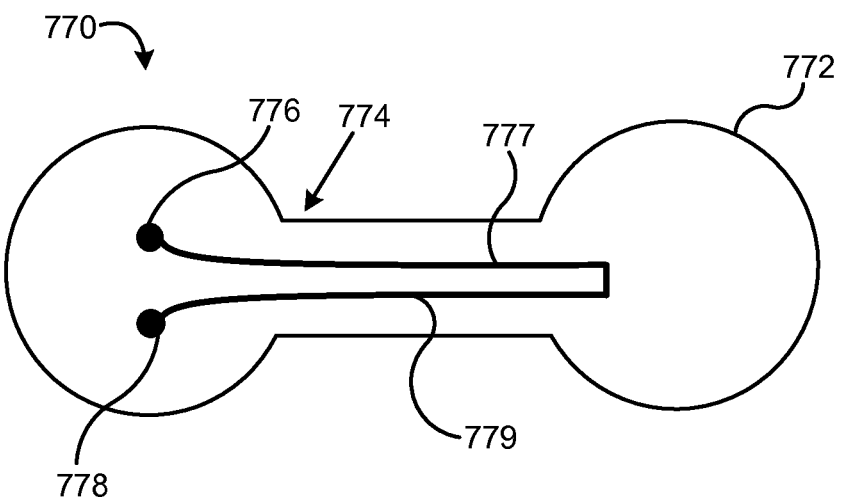

In some embodiments, as illustrated in FIG. 16, an apparatus 770 includes a planar folded dipole antenna coupled to a substrate 772. The antenna 774 includes a first connector 776, a first branch 777, a second connector 778, and a second branch 779. The first connector 776 is configured to be in electrical communication with an external stimulator (not shown). The first branch 777 is configured to electrically couple the first connector 776 to electrical circuitry (not shown) coupled to the substrate 772. The second connector 778 is configured to be in electrical communication with the external stimulator. The second branch 779 is configured to electrically couple the second connector 778 to the electrical circuitry.

Figure 17:
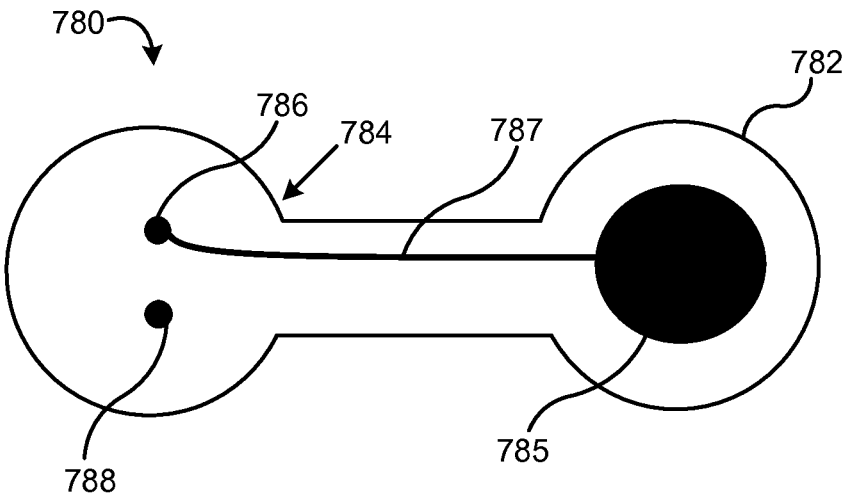

In yet another example, in some embodiments, as illustrated in FIG. 17, an apparatus 780 includes a planar non-symmetrical dipole antenna 784, which may also be referred to as a monopole antenna, coupled to a substrate 782. The antenna 784 includes a first connector 786 and a branch 787. The first connector 786 is configured to be in electrical communication with an external stimulator (not shown). The branch 787 is configured to electrically couple the first connector 786 and electrical circuitry (not shown) coupled to the substrate 782. The branch 787 can be coupled to a power source 785. The antenna 764 includes a second connector 788 configured to be in electrical communication with the external stimulator.

Figure 18:
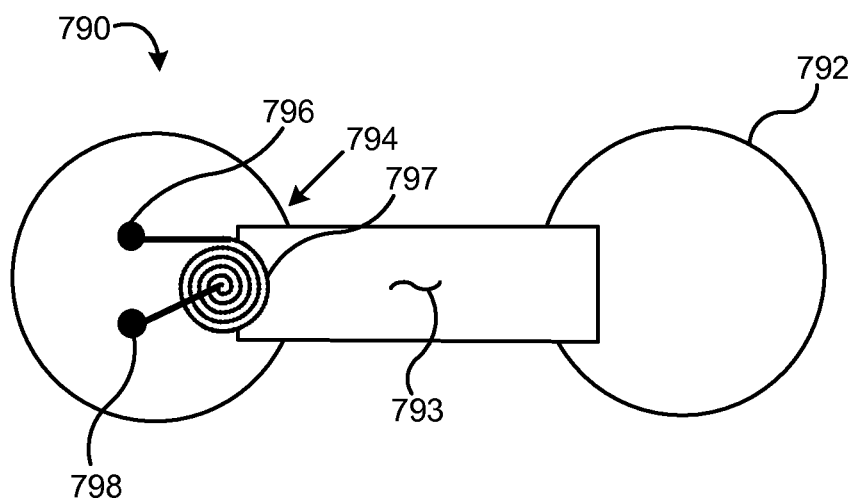

In still another example, in some embodiments, as illustrated in FIG. 18, an apparatus 790 includes a planar spiral antenna 794 coupled to a substrate 792, such as a PCB. The antenna 794 includes a first connector 796, a second connector 798, and an electrical pathway 797. Each of the first connector 796 and the second connector 798 is configured to be in electrical communication with an external stimulator (not shown). The electrical pathway 797 electrically couples the first connector 796 to the second connector 798. The electrical pathway 797 is configured as a spiral at least partially printed on a first surface 793 of the PCB 792. In some embodiments, a return electrical pathway (not shown) can be at least partially printed on an opposing surface (not shown) of the PCB 792. In some embodiments, a return electrical pathway can be at least partially printed on an inner layer of a multi-layered PCB.

Although the apparatus 200, 300, 400, 500, 600, 700 have been illustrated and described as including a power source (or battery) 220, 320, 420, 520, 620, 720, respectively, coupled to a substrate 202, 302, 402, 502, 602, 702, respectively, in some embodiments, an apparatus includes a power source that is the substrate.

Figure 19:
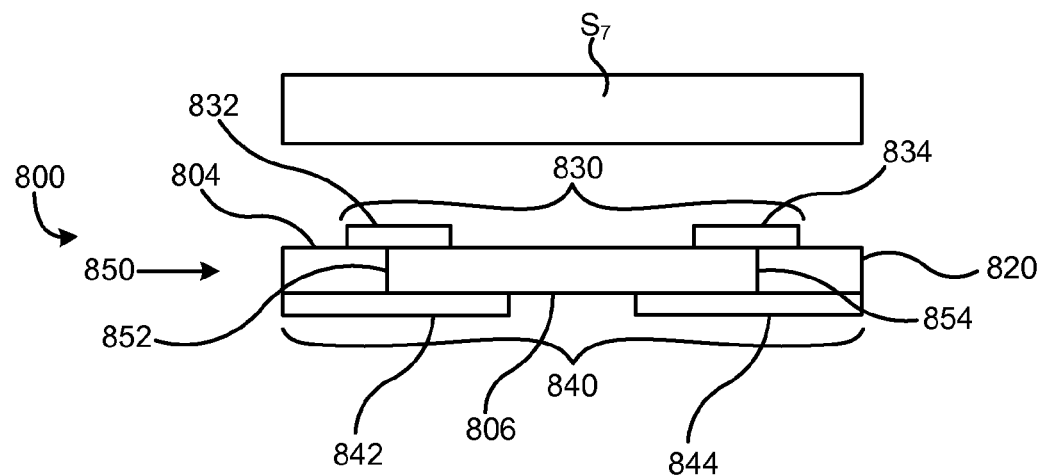
FIG. 19 is a side view of an apparatus according to an embodiment and an external stimulator.

For example, as illustrated in FIG. 19, an apparatus 800 includes a flexible battery 820 having a first surface 804 and a second surface 806. The flexible battery 820 is configured to provide power to an external stimulator $S_7$ coupled the flexible battery 820. The external stimulator $S_7$ can be coupled to the flexible battery by any coupling mechanism described herein that puts the external stimulator in electrical communication with the apparatus 800. For example, as illustrated in FIG. 19, the apparatus 800 includes a connection assembly 830 coupled to the first surface of the flexible battery 820. The connection assembly 830 is configured to complete a power circuit between the flexible battery 820 and the external stimulator $S_7$ and a stimulation circuit between the external stimulator an at least one electrode. The connection assembly 830 includes a first connector 832 and a second connector 834. Each connector 832, 834 is configured to electrically couple the flexible battery 820 to the external stimulator $S_7$. The first connector 832 is configured to electrically couple the external stimulator $S_7$ to a first electrode 842 of an electrode assembly 840 via electrical circuitry 850. The second connector 834 is configured to electrically couple the external stimulator $S_7$ to a second electrode 844 of the electrode assembly via the electrical circuitry 850. The electrode assembly 840 is coupled directly to the second surface 806 of the flexible battery 820. Each of the first electrode 842 and the second electrode 844 is configured to contact a bodily tissue.

In use, when the external stimulator $S_7$ is electrically coupled to the flexible battery 820, the flexible battery provides power to the external stimulator. The external stimulator $S_7$ transmits an electrical output to the first connector 832. The first connector 832 transmits the electrical input as an electrical current to the first electrode 842 via a first electrical pathway 852. The first electrode 842 transmits the electrical current through the bodily tissue to stimulate at least a portion of the bodily tissue. The second electrode 844 receives a portion of the electrical current from the bodily tissue. The second electrode 844 transmits the electrical current to the second connector 834 via a second electrical pathway 854. The second connector 834 transmits an electrical output to the external stimulator $S_7$.

The flexible battery 820 can be biodegradable. In some embodiments, for example, the flexible battery 820 can include a plurality of carbon nanotubes, cellulose disposed between at least a portion of a first carbon nanotube and a second carbon nanotube, an electrolyte, and/or a metal foil of lithium and ion.

While various embodiments have been described above, it should be understood that they have been presented by way of example only, and not limitation. Elements of each embodiment described herein may be combined in any suitable manner with one or more elements of another embodiment described herein. Where methods described above indicate certain events occurring in certain order, the ordering of certain events may be modified. Additionally, certain of the events may be performed concurrently in a parallel process when possible, as well as performed sequentially as described above.

For example, although apparatus 200 is illustrated and described as including a fuse 258, in some embodiments, an apparatus similar to apparatus 200 may include a switch similar to switch 660 in addition to or instead of a fuse.

Although an apparatus has been illustrated and described herein as including one switch or three switches, in other embodiments, an apparatus can include any suitable number of switches, such as two, four, or more switches.

Although a switch has been illustrated and described herein as being in an open configuration in the absence of a magnetic field and as being in a closed configuration in the presence of a magnetic field, in other embodiments, the switch can be differently configured. For example, in some embodiments, a switch can be configured to be in a closed configuration in the absence of a magnetic field and an open configuration in the presence of a magnetic field.

In another example, although an apparatus has been illustrated and described herein as having mechanical connectors for connection to the external stimulator, in other embodiments, such an apparatus can include a wireless connector.

In still another example, although the apparatus have been illustrated and described as including two electrodes, in other embodiments, an apparatus can include any suitable number of electrodes. For example, in some embodiments, an apparatus includes a first cathodic electrode and a plurality of anodic electrodes. The plurality of anodic electrodes can include two, three, four, or more electrodes. Each electrode of the plurality of anodic electrodes can be selectively positioned at a desired location on the body of the patient, such as at spaced locations to help direct an electrical current from the cathodic electrode through a greater area of bodily tissue. In other embodiments, for example, an apparatus can include a first anodic electrode and a plurality of cathodic electrodes. The plurality of cathodic electrodes can transmit a plurality of electrical currents through the bodily tissue to the anodic electrode. In still other embodiments, an apparatus can include a plurality of cathodic electrodes and a plurality of cathodic electrodes.

Figure 20:
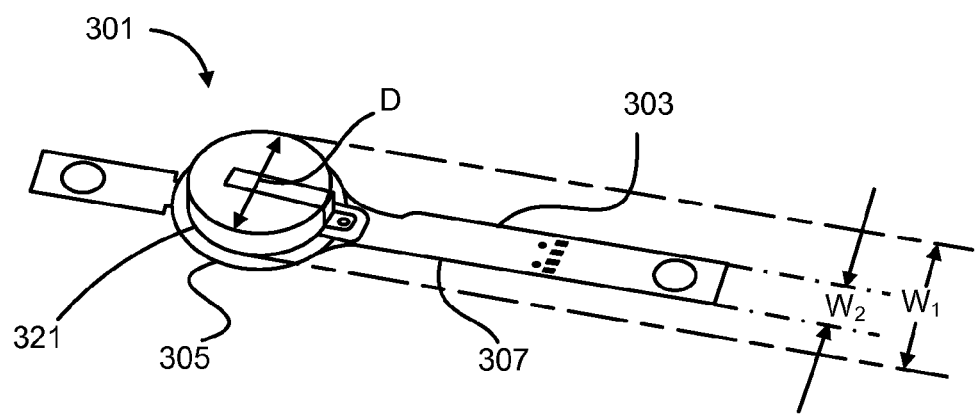
FIG. 20 is a perspective view of an apparatus according to an embodiment.

Although the apparatus have been illustrated and described as including a substrate having a length and a width greater than a length of a first diameter of the power source and a width of a second diameter of the power source, in other embodiments, an apparatus includes a substrate having a different configuration. For example, as illustrated in FIG. 20, an apparatus 301 can include a substrate 303 that has a first portion 305 having a width $W_1$ equal to or greater than a diameter D of the power source 321 and a second portion 307 having a width $W_2$ less than the width $W_1$ of the first portion 305 of the substrate 303.

In yet another example, although the connectors 232, 234, 236 of apparatus 200 have been illustrated and described as having a vertical orientation, in other embodiments, an apparatus can include at least one connector having a different orientation. For example, as illustrated in FIGS. 21-24, an apparatus 900 includes a substrate 902, a power source 920, a connection assembly 930, electronic circuitry 950, an electrode assembly 940, and a coupling mechanism 912 (not shown in FIGS. 21 and 22 for clarity of illustration purposes).

The connection assembly 930 includes connectors 932, 934, 936, 938. Each of the connectors 932, 934, and 938 has a horizontal orientation. In other words, each of the connectors 932, 934, 936, and 938 has an orientation that is substantially parallel to a portion of the substrate 902. In this manner, the external stimulator $S_8$ is moved laterally to engage and/or disengage with the connectors 932, 934, 936, 938 of the apparatus 900.

The connectors 932, 934, 936, 938 are electrically coupled to an electrical pathway 952, 954, 956, 958, respectively, of the electronic circuitry 950. The connectors 932, 934, 936, 938 are configured to electrically couple the electronic circuitry 950 to the external stimulator $S_8$ by being coupled to a counterpart connector $R_1$, $R_2$, $R_3$, $R_4$, respectively, of the external stimulator $S_8$ (see, e.g., FIG. 23).

Figure 24:
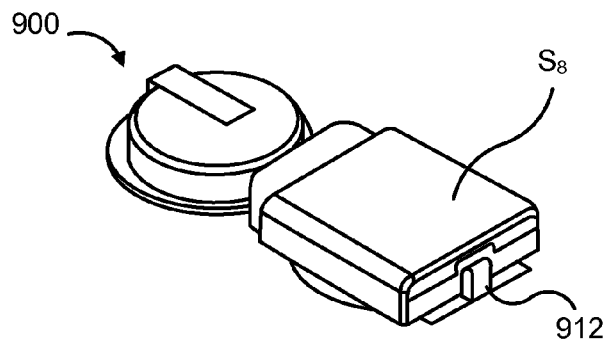
FIG. 24 is a perspective view of the apparatus of FIG. 21 and the external stimulator of FIG. 23.

The coupling mechanism 912 is configured to couple the external stimulator $S_8$ to the apparatus 900. As illustrated in FIG. 24, the coupling mechanism 912 is configured to engage a portion of the external stimulator $S_8$. For example, the external stimulator $S_8$ can define a groove or recess configured to receive a portion of the first member of the apparatus 900. Although the apparatus 900 is illustrated as having the connection assembly 930 coupled to an end of the external stimulator $S_8$ and the coupling mechanism 912 engaged with an opposite end of the external stimulator $S_8$, in other embodiments, the connection assembly and/or the coupling mechanism can engage a different portion of the external stimulator $S_8$.

Figure 21:
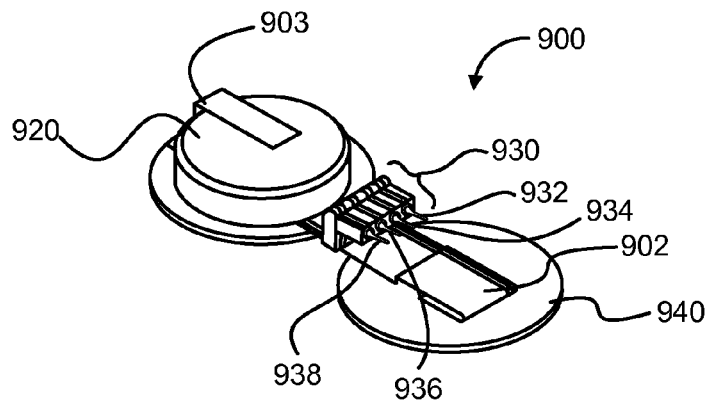
FIG. 21 is a perspective view of a portion of an apparatus according to an embodiment.
Figure 22:
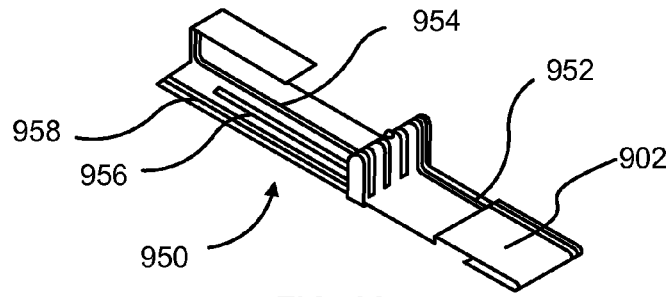
FIG. 22 is a perspective view of a portion of the apparatus of FIG. 21.
Figure 23:
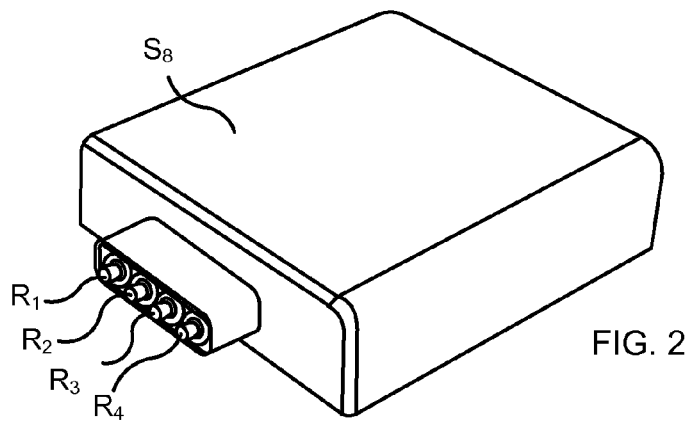
FIG. 23 is a perspective view of an external stimulator configured for use with the apparatus of FIG. 21.

Additionally, although apparatus 200 is shown and described herein as including a power source 220 that is coupled to the PCB 202 by electrically conductive tabs 226, 228, in other embodiments, the power source can be electrically coupled to the substrate in any suitable manner. For example, as illustrated in FIGS. 21-22, a portion 903 of the substrate 902 can be folded or otherwise disposed about a portion of the power source 920. As also illustrated in FIG. 22, a portion of the electrical pathway 954 can be disposed on the portion 903 of the substrate 902 that is folded or otherwise disposed about the portion of the power source 920. When the portion 903 of the substrate 902 is folded about the power source 920, the portion of the electrical pathway 954 contacts the power source 920. In this manner, a terminal of the power source 920 can be electrically coupled to the PCB 202 by the electrical pathway 954.

Figure 25:
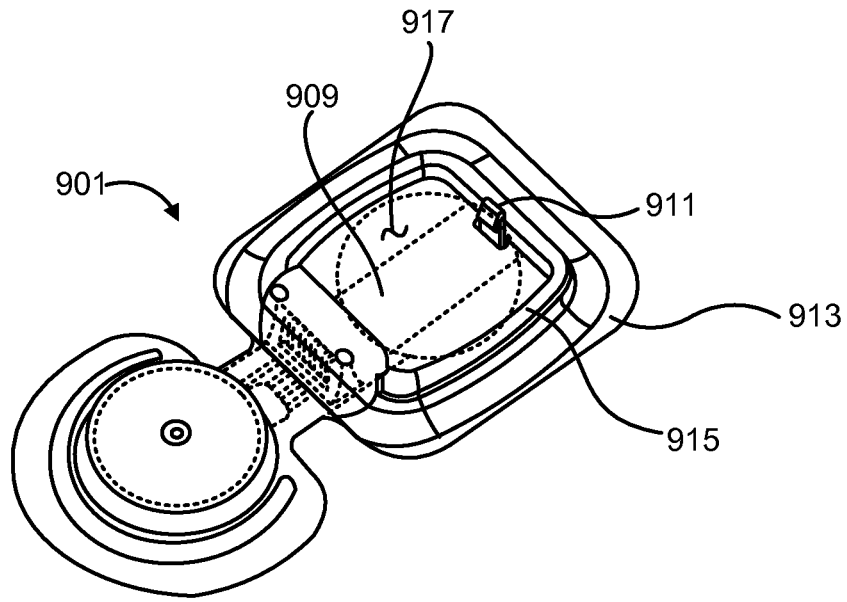
FIG. 25 is a perspective and partially transparent view of an apparatus according to an embodiment.
Figure 26:
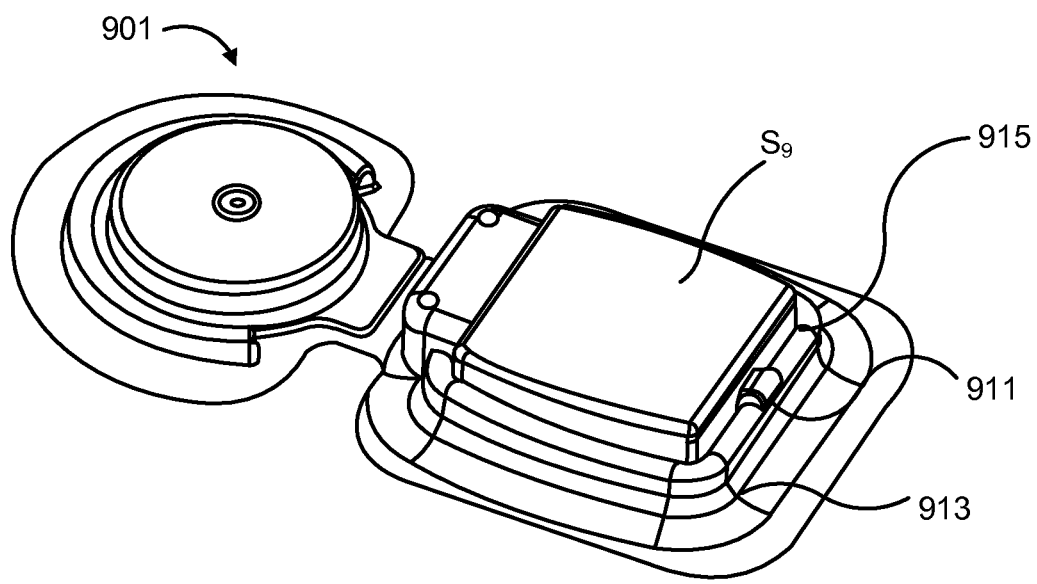
FIG. 26 is a perspective view of the apparatus of FIG. 25 and an external stimulator.

In some embodiments, as illustrated in FIGS. 25 and 26, an apparatus 901 includes a housing 913. The housing 913 is configured to at least partially enclose components (e.g., as shown dashed lines in FIG. 25) of the apparatus 901, such as, but not limited to, a power source, electronic circuitry, a substrate, or the like. The housing 913 defines a perimeter 915 and a recess 917 within the perimeter 915. The recess 917 is configured to at least partially receive an external stimulator $S_9$, as illustrated in FIG. 26. A coupling mechanism 909 (a portion of which is shown in dashed lines in FIG. 25) is configured to removably couple the external stimulator $S_9$ to the housing 913. The coupling mechanism 909 is coupled to the housing 913 and includes a protrusion 911. The protrusion 911 is configured to engage the external stimulator $S_9$ when the external stimulator $S_9$ is at least partially received in the recess 917. The protrusion 911 is configured to release the external stimulator $S_9$ when the protrusion 911 is pushed, depressed, or otherwise moved by the operator (e.g., a physician or the patient). In some embodiments, the protrusion 911 is configured to move the external stimulator $S_9$ in a direction away from the recess 917 when the protrusion 911 is pressed or moved by the operator.

Figure 27:
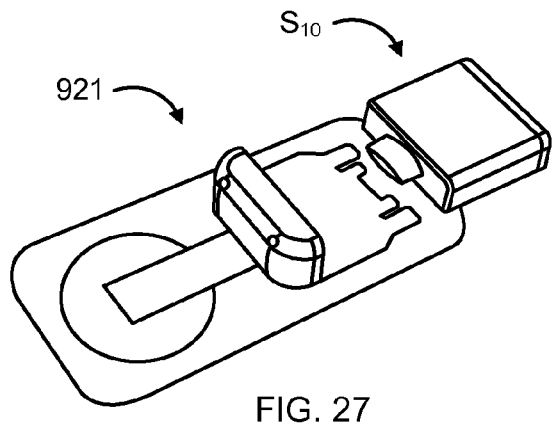
FIG. 27 is a perspective view of an apparatus according to an embodiment and an external stimulator.
Figure 28:
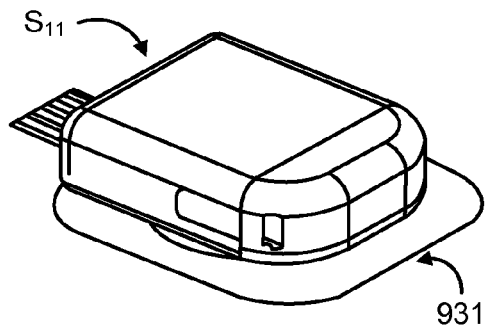
FIG. 28 is a perspective view of a portion of an apparatus according to an embodiment and an external stimulator.

Although the apparatus 900 is illustrated and described herein as including four horizontally oriented connectors 932, 934, 936, 938 configured to be coupled to the external stimulator $S_8$, in other embodiments, an apparatus 921, 931 can be configured to receive a horizontal protrusion of a external stimulator $S_{10}$, $S_{11}$, respectively, as illustrated in FIGS. 27 and 28.

Figure 29:
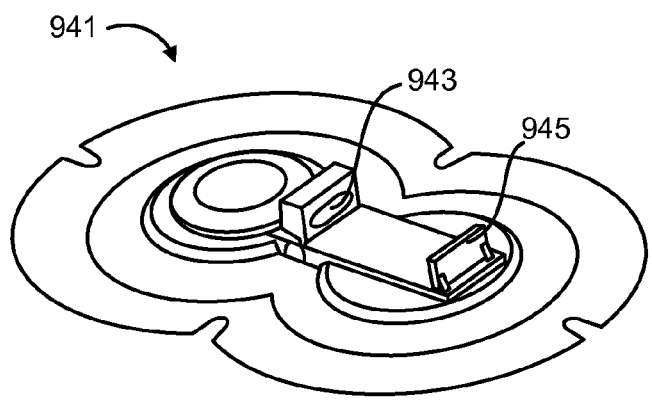
FIG. 29 is a perspective view of an apparatus according to an embodiment.
Figure 30:
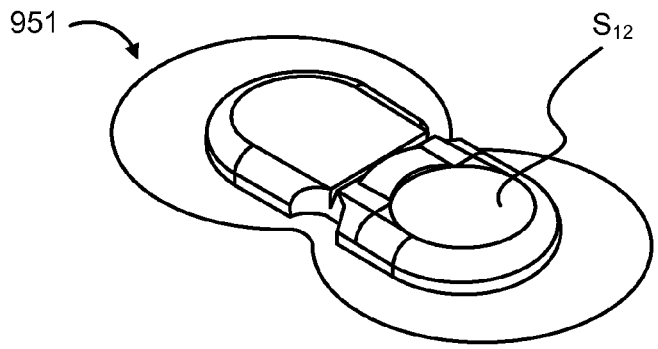
FIG. 30 is a perspective view of an apparatus according to an embodiment and an external stimulator.

In another embodiment, as illustrated in FIG. 29, an apparatus 941 includes a receiving portion 943 configured to receive a portion of an external stimulator $S_{12}$ (not shown) and a protrusion 945 configured to engage an outer surface of the external stimulator $S_{12}$. In still another embodiment, an apparatus 951 is configured to be coupled to an external stimulator $S_{12}$ without such a protrusion, as illustrated in FIG. 30.

Figure 31:
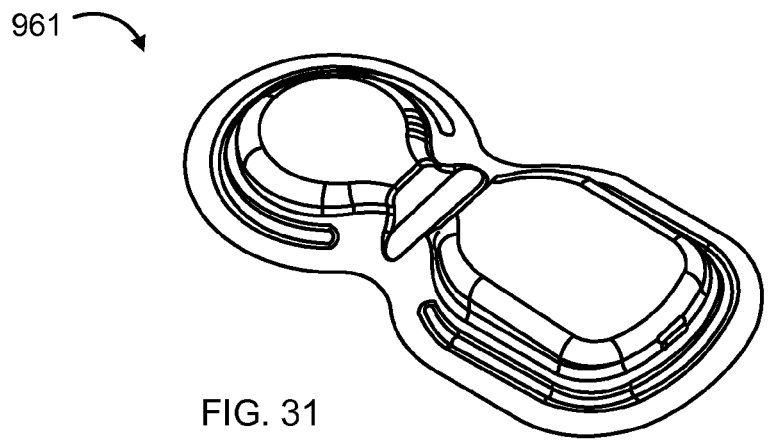
FIGS. 31-33 are perspective views of apparatus according to embodiments and an external stimulator.
Figure 32:
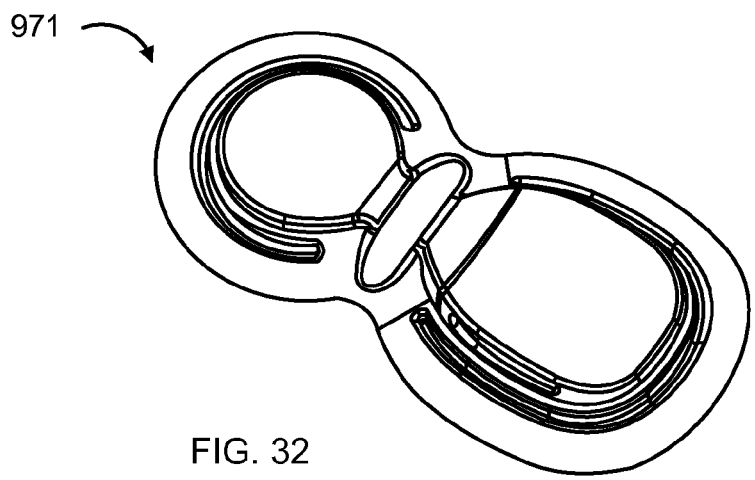
Figure 33:
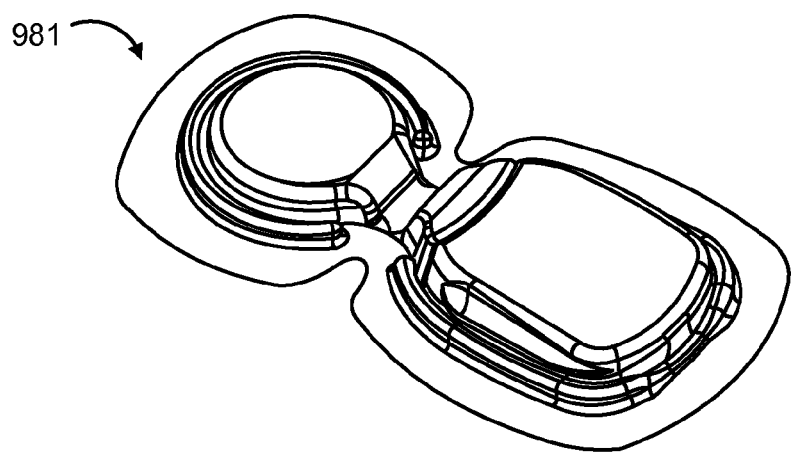

Although the apparatus 901 has been illustrated and described herein as including a housing 913 having a certain outer shape and/or profile, in other embodiments, an apparatus can have a different outer shape and/or profile. For example, an apparatus can include a housing having an outer shape and/or profile like that of apparatus 961, 971, and/or 981, as illustrated in FIGS. 31-33.

Figure 34:
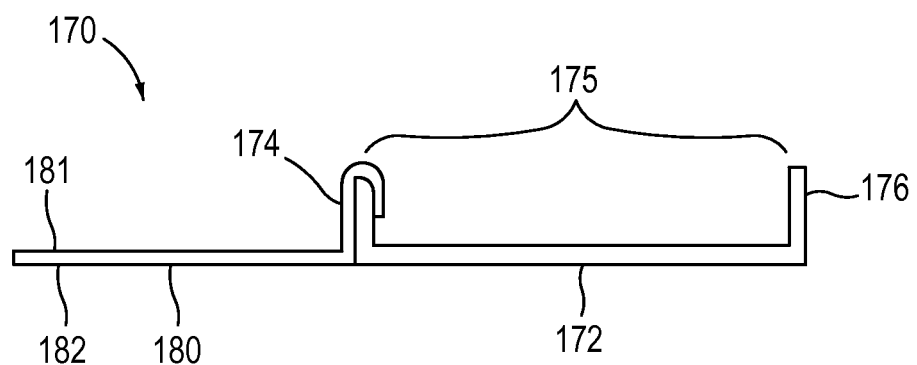
FIG. 34 is a side view of an apparatus according to an embodiment.
Figure 35:
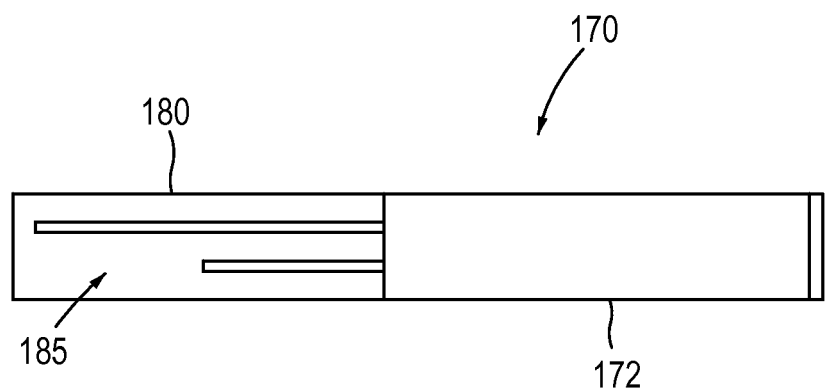
FIG. 35 is a top view of the apparatus of FIG. 34.

Although various embodiments for transmitting an electrical current or stimulation from an electronic device or stimulator to a bodily tissue have been described herein, additional embodiments are contemplated. For example, FIGS. 34-35 show a portion 170 of a stimulation system according to an embodiment. The stimulation system can be any of the stimulation systems shown and described herein, and is configured to transmit an electrical signal or stimulus from a detachable electronic device (not shown) to a bodily tissue of a patient. The portion 170 of the stimulation system can be, for example, a portion of an electrode-battery assembly.

The portion 170 of the stimulation system includes a base 172 and a substrate 180. The base 172 is substantially rigid. An object with substantial rigidity can be characterized as having resistance to deflection and/or deformation in the presence of an external force (e.g., a bending force). The rigidity of an object is an extensive property of the object being described, and thus is dependent upon the material from which the object is formed and certain physical characteristics of the object (e.g., shape and boundary conditions). For example, the rigidity of an object can be increased or decreased by constructing the object from a material having a high modulus of elasticity. The modulus of elasticity is an intensive property of the constituent material and describes an object's tendency to elastically (i.e., non-permanently) deform in response to an applied force. In another example, the rigidity of the object can be increased or decreased by changing the flexural modulus of a material of which the object is constructed. Flexural modulus is used to describe the ratio of the applied stress on an object in flexure to the corresponding strain in the outermost portions of the object. The flexural modulus, rather than the modulus of elasticity, is used to characterize certain materials, for example plastics, that do not have material properties that are substantially linear over a range of conditions. In some embodiments, the base 172 can be constructed from a material having a flexural modulus of at least 750,000 p.s.i.

The base 172 includes a first protrusion 174 and a second protrusion 176. The base 172 is configured to be coupled to the electronic device (not shown in FIGS. 34 and 35). For example, the base 172 can receive at least a portion of the electronic device within the region 175 between the first protrusion 174 and the second protrusion 176. At least one of the first protrusion 174 and the second protrusion 176 can be configured to engage the electronic device when the portion of the electronic device is received by the base 172 (e.g., in a similar manner as described above with respect to protrusion 911 of apparatus 901). The electronic device can be any suitable device including, for example, a stimulator, an external pulse generator, or other electronic device shown and described herein.

The substrate 180 is flexible and is coupled to the base 172. Similarly stated, the substrate 180 has a low resistance to deflection, deformation and/or displacement when exposed to an external force. In this manner, the substrate 180 can be coupled to the base 172 such that the substrate 180 substantially conforms to the shape of one or more portions of the base 172 (e.g., the first protrusion 174). As described herein, this arrangement allows the substrate 180 to be wrapped, woven, and/or otherwise positioned relative to the base 172 in a flexible manner.

The flexibility of the substrate 180 is an extensive property, and thus is dependent upon the properties of the material from which the substrate 180 is constructed as well as certain physical characteristics of the substrate 180 (e.g., shape). For example, the flexibility of the substrate 180 can be increased by constructing the substrate 180 from a material having a low modulus of elasticity and/or a low flexural modulus. In some embodiments the substrate 180 can have a modulus of elasticity and/or a flexural modulus of less than approximately 750,000 p.s.i. In other embodiments the substrate 180 can have a modulus of elasticity and/or a flexural modulus of less than approximately 400,000 p.s.i.

The flexibility of the substrate 180 can also be increased or decreased by changing the shape, cross-sectional area and/or thickness of the substrate 180. Although the substrate 180 is shown as being substantially planar and having a substantially constant thickness, in other embodiments, the substrate 180 can have a non-uniform thickness and/or can have an irregular cross-sectional shape (e.g., corrugations or the like) to result in the desired flexibility. Additionally, to increase the flexibility, the substrate 180 can be thin. In some embodiments, for example, the substrate 180 can have a thickness of approximately 50 to approximately 120 microns (approximately 0.002 to approximately 0.005 inches) or less.

In some embodiments, the substrate 180 can be a polymer, such as a polyester film, a polyimide film, or the like. Such polymers can also include, for example, Mylar®, Kapton® or the like. In other embodiments, the substrate 180 can be a reinforced polymer that includes, for example, a polymer reinforced with glass fibers, graphite fibers, or the like. Such materials can provide the electrical properties (e.g., resistivity and/or conductivity) and the mechanical properties (e.g., toughness, tear resistance, or the like) desired.

The substrate 180 has a first surface 181 and a second surface 182. As shown in FIGS. 34-35, the substrate 180 is coupled to the base 172 such that a first portion of the second surface 182 is in contact with the first protrusion 174. A second portion of the second surface 182 is non-parallel to the first protrusion 174. Said another way, when the substrate 180 is coupled to the base 172, a portion of the substrate 180 is wrapped and/or woven about the first protrusion 174. Similarly stated, when the substrate 180 is coupled to the base 172, a portion of the substrate 180 is non-planar. The flexibility of the substrate 180 facilitates coupling of the substrate to the base 172 such that the substrate 180 is partially disposed about the first protrusion 174.

The substrate 180 includes an electrical circuit 185. The electrical circuit 185 is configured to electronically couple the electronic device to at least one of an electrode, a battery, or an antenna (not shown in FIGS. 34-35). In this manner, for example, the electrode can receive an electrical signal or stimulation from the electronic device via the electrical circuit 185. Also in this manner, the battery can provide power to the electronic device via the electrical circuit 185, for example, to provide sufficient power to the electronic device for the electronic device to generate an electrical signal or stimulation. In another example, the electrical circuit 185 can include the antenna (e.g., an antenna similar to at least one of antennae 614, 616, 764, 774, 784, 794), which can be in wireless electrical communication with the electronic device. In some embodiments, at least one of the electrode, battery, or antenna is coupled to or otherwise disposed on the substrate 180.

Figure 36:
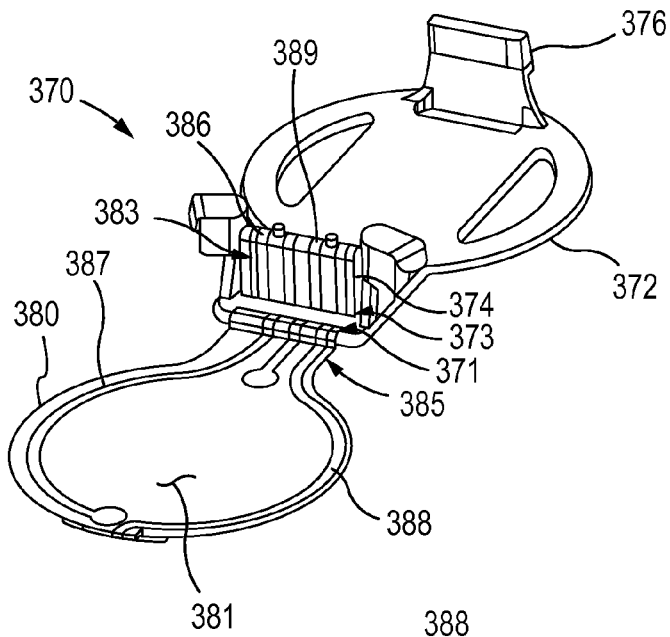
FIGS. 36 and 37 are top and bottom perspective views, respectively, of a portion of a stimulator assembly according to an embodiment.
Figure 37:
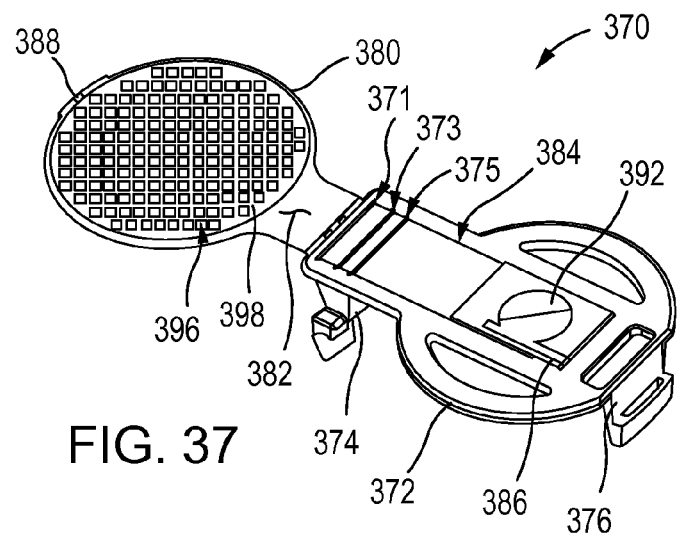
Figure 38:
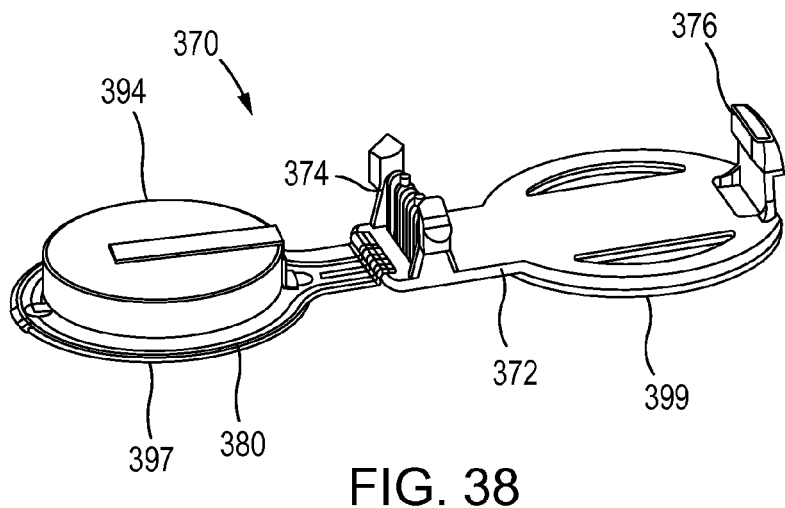
FIG. 38 is a perspective view of the stimulator assembly of FIG. 36 including a battery.

FIGS. 36-38 show a portion of a stimulation system 370 according to an embodiment. The stimulation system can be configured for use with a system to transmit an electrical signal from an electronic device (not shown) to a bodily tissue of a patient. The electronic device can be any suitable electronic device for producing an electrical signal, including any of the electronic devices shown and described herein.

The portion of the stimulation system 370 includes a substantially rigid base 372 and a flexible substrate 380. The flexibility of the substrate 380 facilitates conformance of the substrate 380 to portions of the base 372 and/or to a curvature of a body of the patient. Because the base 372 is substantially rigid, the base is configured to provide structural support to the substrate 380 when the substrate 380 is coupled to the base. The base 372 also has sufficient structural integrity to couple the electronic device to the portion of the stimulation system 370 and/or support the electronic device relative to the stimulation system.

The base 372 includes a first protrusion 374 and a second protrusion 376. The first protrusion 374 and the second protrusion 376 of the base 372 are each configured to maintain contact (e.g., electrical and/or physical contact) between the electronic device and at least the portion the stimulation system 370. For example, at least a portion of the electronic device can be received between the first protrusion 374 and the second protrusion 376 of the base 372. In some embodiments, for example, the first protrusion 374 and the second protrusion 376 are configured to be positioned adjacent a first end portion and a second end portion, respectively, of the electronic device when the electronic device is received between the first protrusion 374 and the second protrusion 376. In some embodiments, the first protrusion 374 and the second protrusion 376 collectively define an interference fit and/or a "snap fit" with the electronic device when the electronic device is received between the first protrusion 374 and the second protrusion 376. In this manner, the first protrusion 374 and/or the second protrusion 376 limit the movement of the electronic device relative to the base 372 when the electronic device is coupled to the base 372. In some embodiments, for example, the first protrusion 374 and/or the second protrusion 376 are configured to matingly engage (e.g., via a tab, recess, detent or the like) a portion of the electronic device. In some embodiments, the second protrusion 376 is engaged with an end of the electronic device when the electronic device is coupled to the base 372 (e.g., as shown and described herein with respect to protrusion 911 of apparatus 901).

The base 372 defines a set of slots including a first slot 371, a second slot 373, and a third slot 375, each being different than the others. Similarly stated, the base 372 defines a series of elongated openings 371, 373, 375 that are distinct and/or non contiguous from each other. In other embodiments, however, the first slot 371, the second slot 373 and/or the third slot 375 can be contiguous and/or can share at least a portion of a common boundary. The first slot 371, the second slot 373 and the third slot 375 each receive a portion of the flexible substrate 380 when the flexible substrate 380 is coupled to the base 372. Similarly stated, the flexible substrate 380 is woven within the first slot 371, the second slot 373 and the third slot 375. More particularly, at least a first portion of the substrate 380 is disposed within the first slot 371 defined by the base, and at least a second portion of the substrate is disposed within the second slot 373 defined by the base, as illustrated in FIGS. 36-37.

The arrangement of the flexible substrate 380 within the first slot 371, the second slot 373 and the third slot 375 results in at least a portion of the flexible substrate 380 being wrapped about the first protrusion 374 of the base 372. In some embodiments, disposal of the substrate 380 within at least one of the slots 371, 373, 375 of the base 380 also serves to couple the substrate to the base 372. Moreover, the arrangement of the flexible substrate 380 within the first slot 371, the second slot 373 and the third slot 375 can be used to index and/or position the substrate 380 relative to the first protrusion 374 in a predetermined position. In this manner, as described in more detail below, a portion of the electrical circuit 385 included within the substrate 380 can be placed in electrical and/or physical contact with the electronic device.

The substrate 380 has a first surface 381 (e.g., an "upper surface") and a second surface 382 (e.g., a "lower surface"). The substrate 380 is coupled to the base 372 such that a first portion 383 of the second surface 382 of the substrate is in contact with the first protrusion 374 of the base. When the substrate 380 is coupled to the base 372, a second portion 384 of the second surface 382 of the substrate 380 is non-parallel to the first portion 383 of the substrate, as illustrated in FIGS. 36-37. For example, in some embodiments, the first portion 383 of the second surface 382 of the substrate 380 is substantially perpendicular to the second portion 384 of the second surface of the substrate 380 when the substrate 380 is coupled to the base 372.

The substrate 380 includes an electrical circuit 385. The electrical circuit 385 can include, for example, any suitable electrical components, via, conductors and/or the like interconnected to perform the functions described herein. More particularly, the electrical circuit 385 includes electrical pathways 387, 386, 389. The electrical pathways can be, for example, conductive traces or metallic strips disposed on the flexible substrate 380. At least a portion of the electrical circuit 385 is included on the first surface 381 of the substrate 380, and is configured to be in electrical communication with the electronic device. For example, the portion of the electrical circuit 385 on the first surface 381 can be complementary to (e.g., on the opposite side of the substrate 380 from) the first portion 383 of the second surface 382 of the substrate 380, such that the portion of the electrical circuit 385 is at least partially disposed about the first protrusion 374 of the base 372. In this manner, for example, the portion of the electrical circuit 385 can be engaged with and/or disposed proximate to an end of the electronic device when the electronic device is coupled to the base 372. When the portion of the electrical circuit 385 is engaged with and/or disposed proximate to an end of the electronic device, the electrical circuit 385 can electrically communicate with the electronic device in any manner described herein, including via wired and/or wireless electrical communication.

The electrical circuit 385 is configured to electronically couple the electronic device to at least one of an electrode, a battery, or an antenna. For example, as illustrated in FIG. 38, the electrical circuit 385 can electronically couple the electronic device to a battery 394 via at least one electrical pathway 387, 389 when the electronic device is coupled to the base 372. More particularly, the battery 394 can be coupled to the first surface 381 of the flexible substrate 380 such that a portion of the electrical pathway 387 is electrically coupled to a first terminal of the battery 394 and a portion of the electrical pathway 389 is coupled to a second terminal of the battery 394. In particular, the portion of the electrical pathway 389 is coupled to a second terminal of the battery 394 by a connector and/or tab similar to the conductive tabs 226, 228 shown and described above. Corresponding terminals of the electronic device (not shown in FIGS. 36-38) are also placed in electrical communication with the electrical pathways 387, 389 when the electronic device is coupled to the base 372 to complete the electronic connection. In this manner, the battery 394 can provide power to the electronic device via the electrical circuit 385 when the electronic device is coupled to the base 372.

The battery 394 can be any suitable battery, such as, for example, a Zinc-Air battery, a Silver-Oxide battery, a Lithium coin battery, a Lithium ion rechargeable battery and/or the like. In embodiments that include a rechargeable battery, the electronic device can be a recharging unit, and can be configured to supply power to the battery 394 via the electrical circuit 385 when the electronic device is coupled to the base 372. Although stimulation system 370 is illustrated and described as including a battery 394, in other embodiments, the stimulation system can include a different source of power, including any source of power shown and described herein.

As illustrated in FIG. 37, the electrical circuit 385 can electronically couple the electronic device to an electrode 392 via an electrical pathway 386. In use, an electrical signal or stimulus can be transmitted from the electronic device through the electrical pathway 386 to the electrode 392. In addition to the electrode 392, the electrical signal or stimulus can be transmitted via the electrical circuit 385 to at least one hydrogel electrode 397, 399 coupled to the second surface 382 of the substrate 380. More particularly, the electrical circuit 385 can electronically couple the electronic device to the hydrogel electrodes 397, 399 (illustrated in FIG. 38), such as via electrical pathway 388 or via electrical pathway 386 and electrode 392, respectively.

At least a portion of the substrate 380 also includes a conductive region 398 and a plurality of non-conductive regions 396. In particular, as illustrated in FIG. 37, the second surface 382 of the substrate 380 can include at least one of the conductive region 398 and the plurality of non-conductive regions 396. For example, at least one of the conductive region 398 and/or the plurality of non-conductive regions 396 can be disposed on the second surface 382 of the substrate 380. As described herein, this arrangement facilitates both the mechanical and electrical coupling of the hydrogel electrode 397 and/or the hydrogel electrode 399 to the substrate 380. In particular, as shown in FIGS. 37 and 38, the conductive and non-conductive regions 398, 396 are configured to contact the hydrogel electrode 397. The conductive region 398 is in electrical communication with the electrical circuit 385, e.g., via the electrical pathway 388. As such, the conductive region 398 is configured to transmit an electrical signal or stimulus from the electrical circuit 385 to the hydrogel electrode 397. In other embodiments, the substrate 380 can include more than one conductive region 398 and plurality of non-conductive regions. For example, in some embodiments, the substrate can include a second conductive region (not shown) and a second plurality of non-conductive regions (not shown) configured to place the hydrogel electrode 399 in electrical communication with the electrical circuit 385, e.g., via the electrical pathway 386.

In some embodiments, the plurality of non-conductive regions 396 is included within and/or adjacent the conductive region 398. For example, the plurality of non-conductive regions 396 can be disposed on a surface of the conductive region 398. Each non-conductive region of the plurality of non-conductive regions 396 is discrete from the other non-conductive regions of the plurality. At least one non-conductive region of the plurality of non-conductive regions 396 extends beyond (or away from) a surface of the conductive region 398. Said another way, at least one non-conductive region of the plurality of non-conductive regions 396 is substantially non-planar with the conductive region 398. Said yet another way, at least one non-conductive region of the plurality of non-conductive regions 396 forms a surface textured area on the conductive region 398 of the substrate 380. In this manner, when the hydrogel electrode 397 is in contact with the substrate 380, the plurality of non-conductive regions 396 and the conductive region 398 collectively reduce the likelihood that the hydrogel electrode 397 will peel or otherwise move away from the conductive region 398 of the substrate 380 (e.g., in the presence of shearing forces). As such, the plurality of non-conductive regions 396 is configured to facilitate coupling and/or the mechanical connection, between the hydrogel electrode 397 and the substrate 380. Said another way, the plurality of non-conductive regions 396 is configured to facilitate retention of the hydrogel electrode 397 with respect to the conductive region 398 of the substrate 380.

Further, because each discrete non-conductive region of the plurality 396 is surrounded on its perimeter by the conductive region 398, an electrical current can be evenly distributed through the hydrogel electrode 397. Even distribution of the electrical current from the conductive region 398 of the substrate 380 through the hydrogel electrode 397 can reduce and/or prevent electrical "hotspots" (i.e., areas of concentrated electrical stimulation that can cause skin irritation and/or uncomfortable sensations to a patient).

The plurality of non-conductive regions 396 can be formed in any suitable manner. For example, in some embodiments, at least one non-conductive region of the plurality of non-conductive regions 396 is a solder mask. Use of a solder mask to form the plurality of non-conductive regions 396 on the conductive region 398 permits the plurality of non-conductive regions to be formed in any suitable desired pattern on the conductive region 398. Any known suitable method and/or material for producing the solder mask may be used. In another example, at least one non-conductive region is formed by a coating applied to the surface of the conductive region 398.

Although the plurality of non-conductive regions 396 have been described herein as being disposed on the conductive region 398 of the substrate 380, in other embodiments, the plurality of non-conductive regions can be included within and/or adjacent the conductive region in any suitable manner. For example, at least one non-conductive region of the plurality of non-conductive regions can be a cavity or other depressed portion formed in a surface of the conductive region of the substrate. The cavity can be configured to receive a portion of the hydrogel electrode, thereby facilitating retention of the hydrogel electrode with respect to the conductive region of the substrate. In some embodiments, the cavity is formed by etching one or more discrete portions of the conductive region. For example, in some embodiments, the conductive region includes a metal layer disposed on or otherwise coupled to the substrate and the plurality of non-conductive regions is formed by etching away discrete portions of the metal layer. In another example, at least one non-conductive region of the plurality of non-conductive regions can be an aperture or other opening defined by the conductive region of the substrate. Such an aperture or other opening can be formed, for example, by punching the aperture or other opening in the conductive region of the substrate with a mechanical punch. The aperture can be configured to receive a portion of the hydrogel electrode, thereby facilitating retention of the hydrogel electrode with respect to the conductive region of the substrate. Although various manners for forming the non-conductive regions have been described herein, the plurality of non-conductive regions can be formed in any suitable manner, including any combination of the foregoing manners.

Each non-conductive region of the plurality of non-conductive regions 396 can be of any suitable size and/or shape. For example, as illustrated in FIG. 37, at least one non-conductive region of the plurality of non-conductive regions 396 can be in the shape of square (or a three-dimensional cube). The at least one non-conductive region can be, for example, a 1 mm×1 mm square. In other embodiments, at least one non-conductive region can be rectangular, triangular, oval, circular, or any other suitable shape. Additionally, the at least one non-conductive region can have dimensions of a size different than 1 mm×1 mm, such as a length, width, and/or cross-sectional diameter of greater than approximately 1 mm (e.g., approximately 2 mm to approximately 4 mm) or less than approximately 1 mm (e.g., approximately 0.3 mm to approximately 0.8 mm).

Although the portion of the substrate 380 including the conductive region 398 and the plurality of non-conductive regions 396 is illustrated and described as having a substantially circular shape, in other embodiments, the portion of the substrate can have any suitable shape. For example, in some embodiments, the portion of the substrate can be oval, rectangular, square, or another suitable shape.

Additionally, the portion of the substrate 380 including the conductive region 398 and plurality of non-conductive regions 396 can be of any suitable size. For example, the portion of the substrate 380 can have a diameter of approximately 30 mm. In another embodiments, the portion of the substrate can have a diameter of less than 30 mm (e.g., a diameter within the range of approximately 10 mm to approximately 30 mm). In still other embodiments, the portion of the substrate can have a diameter of greater than 30 mm (e.g., a diameter within the range of approximately 30 mm to approximately 60 mm).

The substrate 380 can be constructed of any suitable material. In some embodiments, for example, the substrate 380 is a flexible PCB. In another example, the substrate can be constructed of a different material, including silicon, polyamide, or another suitable polymer, or any combination of the foregoing.

Although stimulation system 370 is illustrated and described as having one portion of the substrate 380 including the conductive region 398 and the plurality of non-conductive regions 396 associated with the hydrogel electrode 397, in other embodiments, an apparatus can include more than one conductive region and more than one plurality of non-conductive regions. For example, in other embodiments, the substrate can include a number of conductive region and a number of non-conductive regions corresponding to, or equivalent to, the number of hydrogel electrodes to be utilized with the apparatus (e.g., two, three, or more).

FIGS. 39-42 show portions of a stimulator assembly 495 according to an embodiment. In particular, the stimulator assembly 495 includes a battery 494, an electrode 497, a stimulus generator 490, a substrate 480, a base 472 and a housing 465. The stimulator assembly 495 can be used to transmit an electrical current from the stimulus generator 490 to a bodily tissue of a patient. Components of the stimulator assembly 495 can be similar in many respects to components of apparatus shown and described herein (e.g., components of electrode-battery assembly 100, apparatus 200, stimulation system 370, 570).

The housing 465, which is a substantially flexible housing, is configured to be disposed about at least a portion of a stimulator assembly 495 (e.g., the base 472). Similarly stated, the housing 465 has a low resistance to deflection, deformation and/or displacement when exposed to an external force. In this manner, the housing 465 can be disposed about other portions of the stimulator assembly 495 such that the housing 465 substantially conforms to the shape of one or more of the other portions of the stimulator assembly (e.g., the protrusion 476, the stimulus generator 490, or the like). In some embodiments, the flexible housing 465 is configured to substantially prevent access of moisture to the portion of the stimulator assembly 495 about which the flexible housing 465 is disposed.

The flexible housing 465 includes a receiving portion 466, which is configured to receive at least a portion of the stimulus generator 490. The receiving portion 466 defines a first opening 468 (see FIG. 40) and a second opening 469 (see FIG. 39) different than the first opening. The first opening 468 is configured to receive a protrusion 491 of the stimulus generator 490. The protrusion 491 of the stimulus generator 490 can include, for example, one or more electrical contacts 493 configured to place the stimulus generator 490 in electrical communication with other portions the stimulator assembly 495 (e.g., the battery 494, the electrode 497). The electrical contacts 493 can be any suitable mechanism for electrically coupling the stimulus generator 490 with other portions the stimulator assembly 495. In some embodiments, the electrical contacts 493 are biased to help retain the stimulus generator 490 to the housing 465 and/or the stimulator assembly 495. For example, the electrical contacts 493 can include a spring, which may also be configured to transmit an electrical current between the stimulus generator 490 and the stimulator assembly 495, an elastomer, or other suitable biasing mechanism, or any combination of the foregoing.

The second opening 469 of the flexible housing 465 is configured to receive a protrusion 476 of the base 472. The base 472 can be similar to the base 372 and/or the base 172 shown and described above. As described in more detail herein, the protrusion 476 of the base 472 is configured to couple the stimulus generator 490 to the housing 465 and other components of the stimulator assembly 495. Although the first and second openings 468, 469 of the housing 465 are illustrated as being defined by opposing ends of the receiving portion 466, in other embodiments, the first opening and/or the second opening can be defined by a different portion of the receiving portion.

Figure 39:
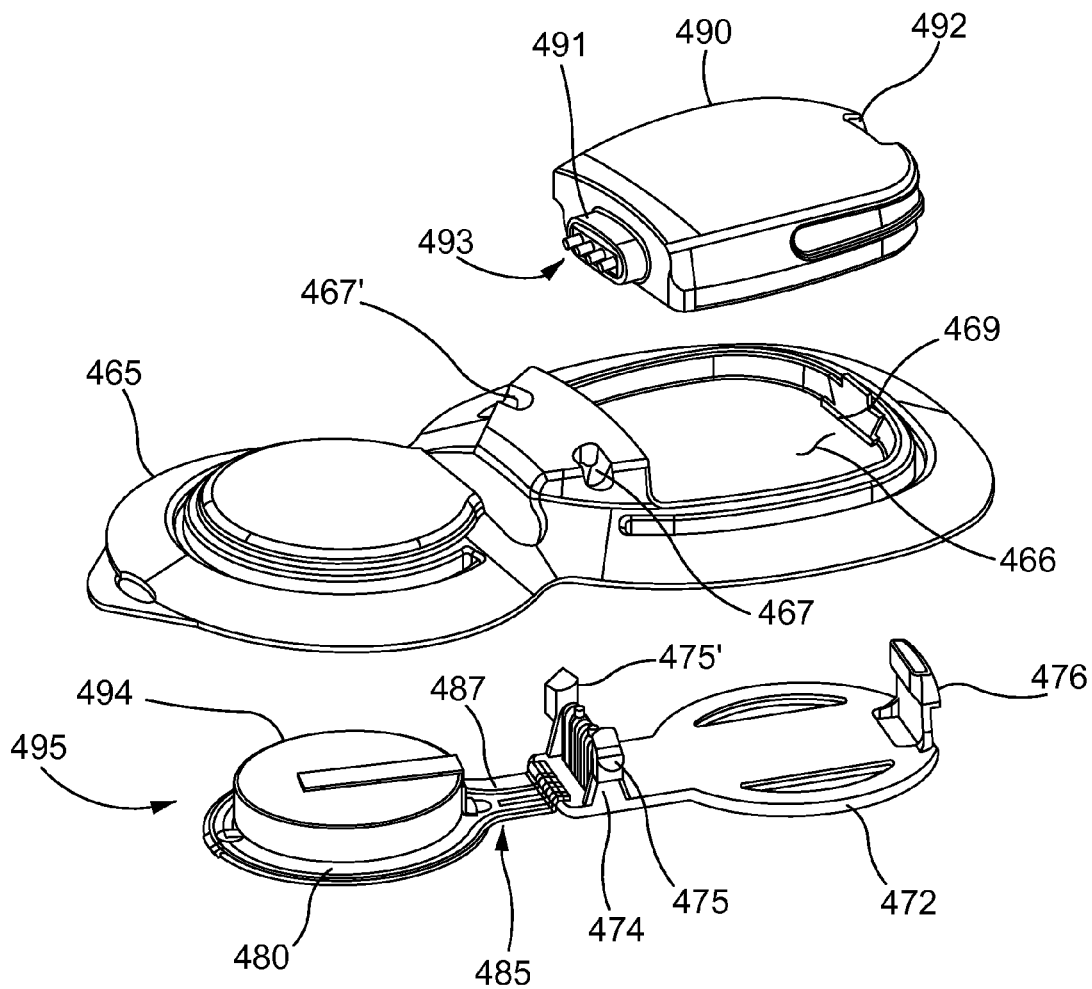
FIG. 39 is an exploded perspective view of a stimulator assembly according to an embodiment.
Figure 40:
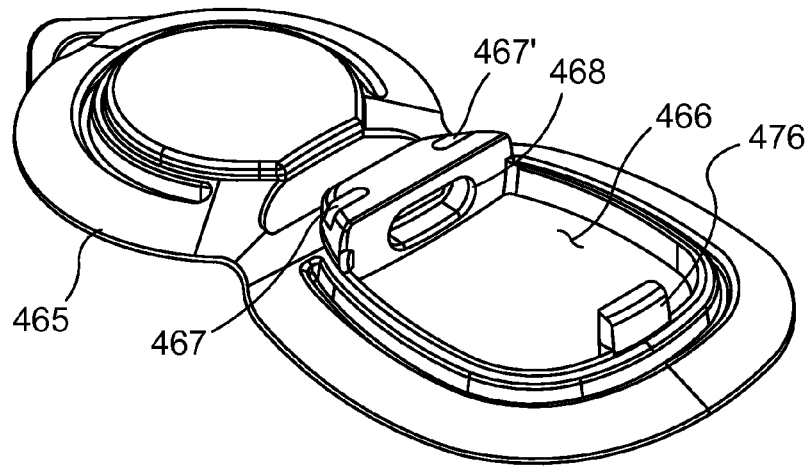
FIG. 40 is a perspective view of a portion of the stimulator assembly shown in FIG. 42.
Figure 41:
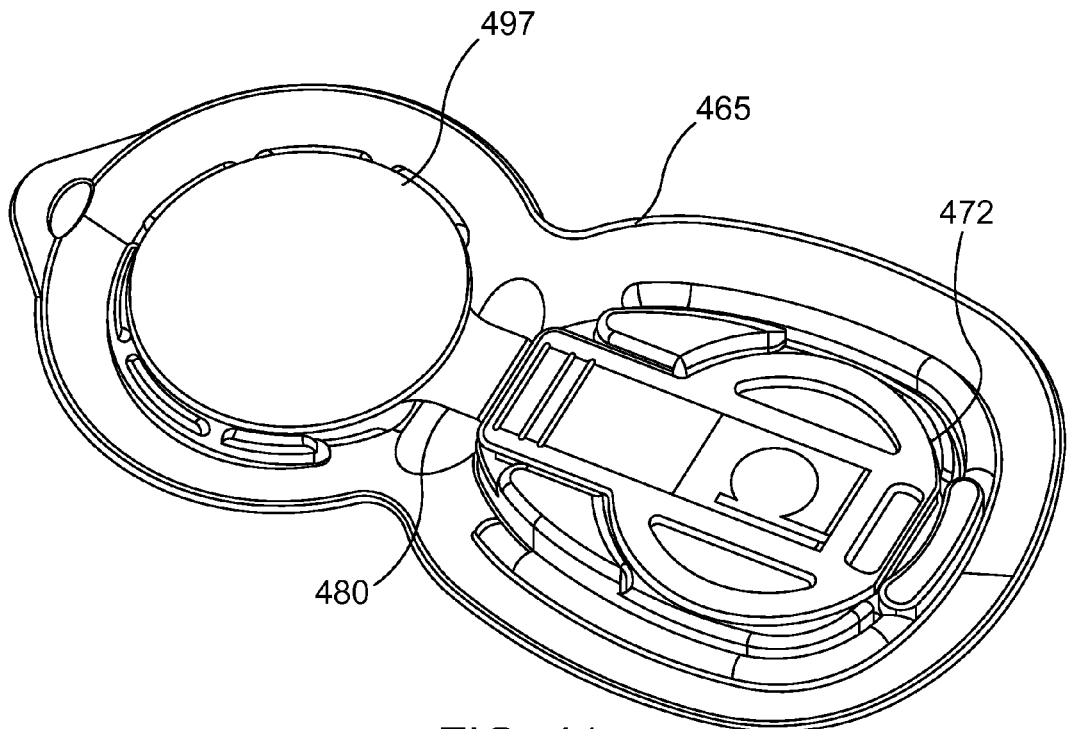
FIG. 41 is a bottom view of the stimulator assembly of FIG. 39.
Figure 42:
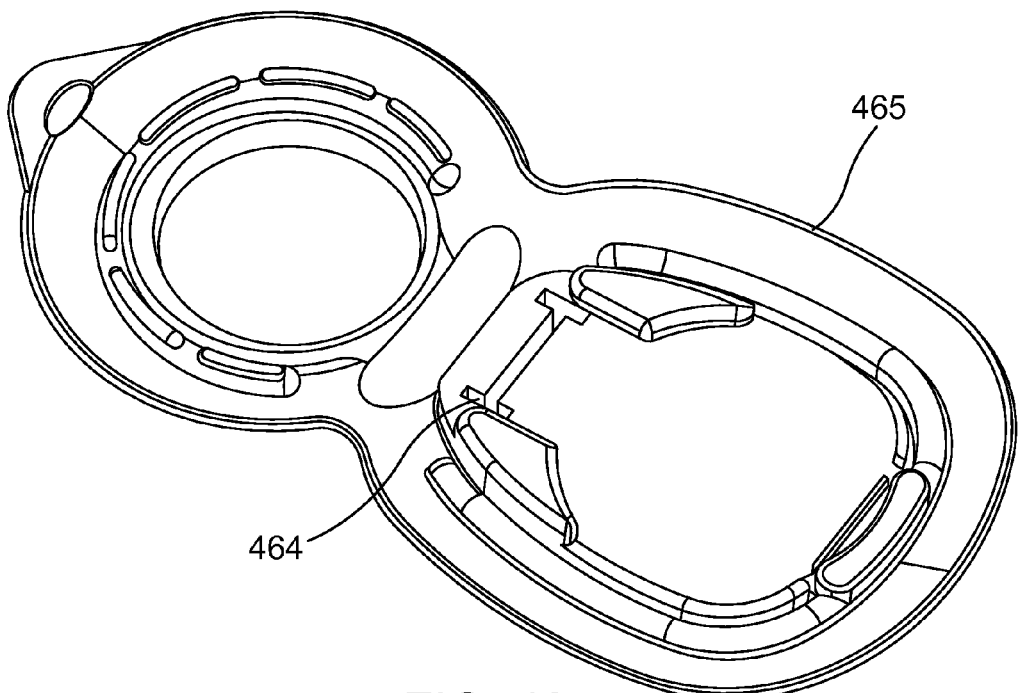
FIG. 42 is a top view of the stimulator assembly of FIG. 39 with a portion of the housing removed.

As shown in FIG. 42, the housing 465 also defines a recess 464 configured to receive a fastening member 474 (shown in FIG. 39) of the base 472. A portion of the housing 465 has been removed in FIG. 42 for illustrative purposes only. The fastening member 474 can include end portions 475, 475', each of which are configured to be received in respective openings 467, 467' defined by the housing 465. The end portions 475, 475' are each configured to facilitate coupling of the housing 465 to the stimulator assembly 495 when the end portions 475, 475' are received in the openings 467, 467'. As such, when the flexible housing 465 is disposed about at least a portion of the stimulator assembly 495 and the fastening member 474 is received in the recess 464, as illustrated in FIG. 40, movement of the housing 465 relative to other portions of the stimulator assembly 495 is limited. In other words, the fastening member 474 is configured to couple or fasten the housing 465 to the other portions of the stimulator assembly 495 in a manner such that the lateral and/or vertical movement of the housing 465 with respect to the stimulator assembly 495 in the presence of substantially normal physical activities (e.g., walking, bathing, or the like) is substantially restricted.

When the fastening member 474 fastens the housing 465 to the remainder of the stimulator assembly 495, the protrusion 476 of the base 472 is received within the opening 469 of the receiving portion 466. The protrusion 476 is configured to limit movement of the stimulus generator 490 with respect to the housing 465 when the stimulus generator is received in the receiving portion 466 of the housing. In use, when the stimulator generator 490 is received in the receiving portion of the housing 465 and the protrusion 491 of the stimulus generator is received in the opening 469, the protrusion 476 of the base 472 engages a portion of the stimulus generator 490. For example, as illustrated in FIG. 39, the protrusion 476 engages a recess 492 defined by the stimulus generator 490 when the stimulus generator 490 is received in the receiving portion 466 of the housing 465. In some embodiments, the protrusion 476 is resiliently biased towards the portion of the stimulus generator 490. In this manner, the protrusion 476 retains the stimulus generator 490 with respect to the housing 465 when the stimulus generator 490 is received in the receiving portion 466 of the housing, and thus limits movement of the stimulus generator 490 with respect to the housing 465. Said another way, the resistance that occurs by engagement of the protrusion 476 with the portion of the stimulus generator 490 facilitates coupling of the stimulus generator 490 to the housing 465. The protrusion 476 is configured to release the stimulus generator 490 when the protrusion 476 is pushed, depressed, or otherwise moved by the operator (e.g., a physician or the patient).

Although the recess 492 is illustrated as being on an end of the stimulus generator 490 that is opposite to an end of the stimulus generator including the protrusion 491, in other embodiments, the recess (or other portion configured to engage protrusion 476) can be defined by a different portion of the stimulus generator.

When the stimulus generator 490 is received in the receiving portion 466 and the protrusion 491 of the stimulus generator is received in the opening 468, the stimulus generator 490 is electrically coupled to the battery 494. In some embodiments, the stimulus generator 490 is electrically coupled to the battery 494 via an electrical circuit 485 disposed on the substrate 480 in a similar manner as described above with reference to the portion of the stimulation system 370. The electrical circuit 485 includes at least one electrical pathway 487. More particularly, when the protrusion 491 of the stimulus generator is received in the opening 468, the electrical contacts 493 are placed in contact with the electrical circuit 485. The battery 494 is also in electrical connection with the electrical circuit 485, as described above, and thus the battery 494 is placed in electrical communication with the stimulus generator 490. In other words, the electrical circuit 485 electrically couples the stimulus generator 490 to the battery 494. The electrical circuit 485 can also electrically couple the stimulus generator 490 to the electrode 497, as described above. The housing 465 is configured to substantially maintain the stimulus generator 490 in electrical communication with the electrical circuit 485 when the stimulus generator 490 is received in the receiving portion 466 and the housing 465 is disposed about at least a portion of the substrate 480 of the stimulator assembly 495.

A portion of the housing 465 is configured to form a substantially fluid-tight seal proximate to the receiving portion 466 when the at least a portion of the stimulus generator 490 is received in the receiving portion 466. In some embodiments, the housing 465 can form a seal to substantially prevent passage of a fluid from an area exterior to the housing and the stimulus generator 490 to an area interior to the housing 465 and/or an area between the housing 465 and the stimulus generator 490 (e.g. between a perimeter of the receiving portion 466 and the stimulus generator). In another example, the housing 465 can form a seal about the opening 468 when the protrusion 491 of the stimulus generator 490 is received in the opening to substantially prevent passage of a fluid therethrough. The fluid can be, for example, a liquid, a slurry, a gas, or the like. Thus, the housing 465 and/or the stimulator assembly 495 can be characterized as being water-resistant.

The housing 465 can be constructed from any suitable material to provide the desired flexibility, sealing properties or the like. In some embodiments, the housing 465 can be constructed from a polymer or rubber compound having a modulus of elasticity and/or a flexural modulus of less than approximately 750,000 p.s.i. In some embodiments, the housing 465 can be constructed of an elastomer. The elastomer can be injection molded, e.g., from a bio-compatible material. In some embodiments, the elastomer has a mechanical elasticity of about 40 Shore D. Thus, the housing is soft and flexible, which facilitates compliance with a curvature of the patient's body and which facilitates accurate positioning of rigid parts of the stimulator assembly 495 (e.g., the battery 494, the stimulus generator 490) on the patient's body. For example, in some embodiments, the housing 465 exhibits a degree of flexibility that permits the housing 465 to be placed substantially about a surface of a radial body part of the patient (e.g., an arm, a leg, or other limb). Although the housing 465 is described herein as being constructed of an elastomer, in other embodiments, the housing 465 can be constructed of any suitable material, including, for example, a silicon, polyamide, or another suitable polymer, or any combination of the foregoing.

The housing 465 can be disposed on or coupled to the body of the patient in any suitable known manner. For example, the housing 465 can be coupled to the body using a medical plaster, which may be beneficial for larger bodily areas, including an abdomen or a backside of a shoulder. In another example, the housing 465 can be coupled to the body of the patient using a band, which may be beneficial for parts of the patient's body having a substantially circular cross-section (e.g., the arm, leg, or other limb). Use of the band also permits easy attachment, detachment, and repositioning of the housing 465 on the body of the patient.

Figure 52:
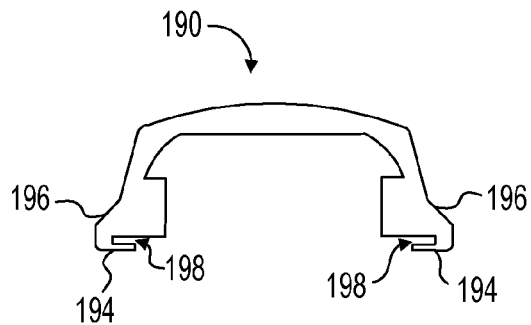
FIG. 52 is a front, cross-sectional view of a portion of a housing according to an embodiment.

In some embodiments, as illustrated in FIG. 52, a housing 190 can be configured to prevent migration and/or displacement of an electrode (e.g., a hydrogel electrode, not shown in FIG. 52) with respect to the housing in the presence of a shearing force and/or a mechanical stress. The housing 190 includes a flange 194 that extends from a body portion 196 of the housing to form a channel 198. In some embodiments, as illustrated in the cross-sectional view of the housing 190 shown in FIG. 52, the flange 194 forms a substantially continuous rim about a lower portion of the body portion 196 of the housing 190. In other embodiments, however, the housing can include a plurality of discrete flanges, which collectively form a discontinuous and/or non-contiguous rim about the lower portion of the body portion of the housing. For example, the housing can include two or more flanges disposed on the body portion at spaced (e.g., opposing) locations.

The channel 198 is configured to receive a portion of the periphery (or edge) of the electrode. In the embodiment illustrated in FIG. 52, the channel 198 is substantially U-shaped, however, in other embodiments, the channel can be any suitable shape for receiving a portion of the periphery of the electrode. When the peripheral portion of the electrode is received in the channel 198 of the flange 194, lateral movement of the electrode relative to the housing is restricted. In this manner, the housing 190 is configured to couple the electrode to the housing, and thus to a stimulator assembly (not shown in FIG. 52) to which the housing is attached.

Although the flange 194 and channel 198 have been illustrated and described herein as being integrally formed with the housing 190, in other embodiments, the electrode rim, or a portion thereof, can be manufactured as a separate and distinct portion that is couplable to the housing.

Figure 53:
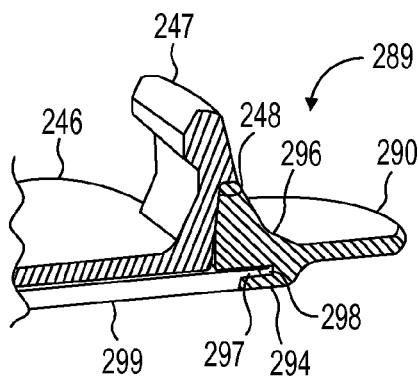
FIG. 53 is a perspective, cross-sectional view of a portion of a stimulator assembly according to an embodiment.

Further, although the housing 190 has been illustrated and described herein as including the electrode rim, in other embodiments, the electrode rim can be included in or coupled to a different portion of the stimulator assembly. For example, as illustrated in FIG. 53, a stimulator assembly 289 includes a rim 290, which is removably couplable to a base 246 of the stimulator assembly, as described herein. The rim 290 includes a body portion 296 and a flange 294. The flange 294 of the rim 290 is extended from the body portion 296 and forms a channel 298 between the flange and the body portion. The flange 294 is disposed about a portion of a periphery of at least one electrode 299 (e.g., a hydrogel electrode) such that a portion of the electrode's periphery 297 is received in the channel 298. In some embodiments, the electrode 299 is fixedly received in the channel 298 of the rim 290. In other embodiments, the electrode 299 is removably received in the channel 298 of the rim 290. The electrode 299 can be disposed within the channel 298 of the rim 290 during the manufacturing process, e.g., to permit distribution of the electrode and rim in a single package. As illustrated in FIG. 53, a protrusion 247 of the base 246 includes a recess 248 that is configured to receive a portion of the body portion 296 of the rim 290, and thus is configured to couple the rim 290 and electrode 299 to the base 246. As such, the rim 290 facilitates attachment, removal and/or replacement of the electrode 299 with respect to the stimulator assembly 289.

Although the rim 290 is shown and described above as being coupled to the base using recess 248 of the protrusion 247 of the base, in other embodiments, the rim 290 can be differently coupled to the base. For example, in some embodiments, the rim 290 can be coupled to the base with an elastic configured to be disposed about a portion of the base, a clip, a hook and loop fastener, or an adhesive, or any combination of the foregoing.

Further, in other embodiments, the electrode rim can be configured to be coupled to a different portion of a stimulator assembly, including, but not limited to, a substrate of the stimulator assembly. In still other embodiments, an electrode rim can integrally formed with a base, substrate, or other suitable portion of a stimulator assembly.

FIGS. 43-47 illustrate a portion of a stimulation system 570 according to an embodiment. The portion of the stimulation system 570 is configured to deliver an electrical current from an electronic device (not shown) to a bodily tissue of a patient. The portion of the stimulation system 570 includes a substrate 580, a power source 594, a casing 592, electrodes 597, 599, an electrical circuit 585, a coupling member 572, and a housing 565, each of which are coupled to or otherwise disposed on the substrate 580.

The substrate 580 is flexible such that the substrate can substantially conform to the contours of the portion of the patient's body on which the portion of the stimulation system 570 is disposed. For example, the substrate 580 can be configured to be flexible such that the substrate conforms to the curvature of a patient's arm, leg, or back. In this manner, the substrate 580 is configured to facilitate positioning and placement of the stimulation system on the patient's body. In some embodiments, the substrate 580 can be similar to and/or constructed from similar materials as any of the substrates shown and described herein.

The substrate 580 has a first configuration and a second configuration different than the first configuration. In its first configuration, the substrate 580 has a first area (see, e.g., FIG. 45). Similarly stated, when the substrate 580 is in its first (or unfolded) configuration, the substrate 580 occupies a first surface area and/or defines a first "footprint." When the substrate 580 is in its first configuration, each of the electrodes 597, 599 and the electrical circuit 585 face a first direction and are disposed on a first side 581 of the substrate. For example, when the substrate 580 is in its first configuration and the substrate is positioned horizontally, the electrodes 597, 599 and the electrical circuit 585 can be characterized as facing "up."

Figure 45:
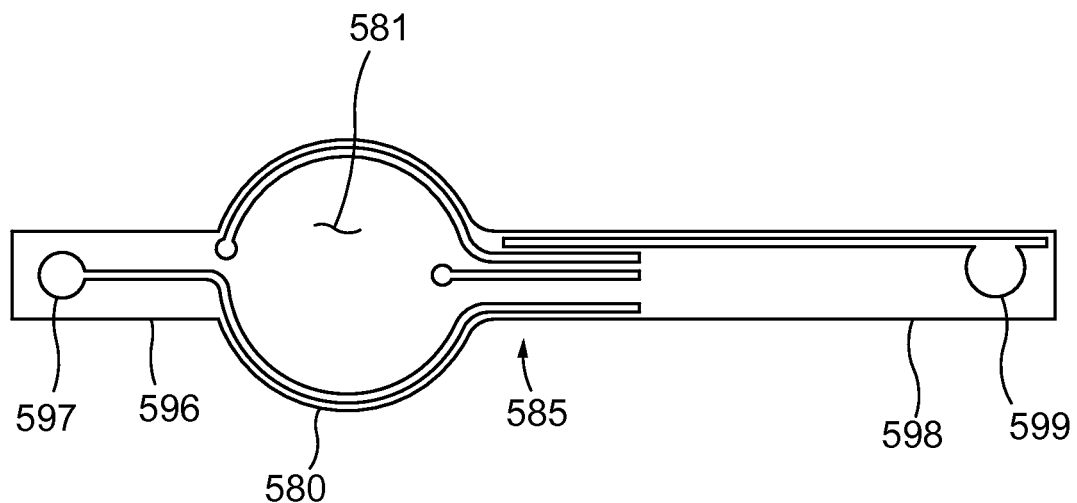
FIG. 45 is a top view of a portion of the stimulator assembly of FIG. 43 in a first configuration.
Figure 46:
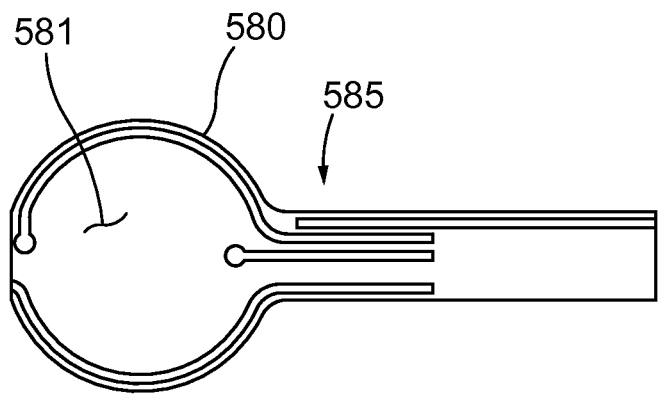
FIGS. 46-47 are top and bottom views, respectively, of a portion of the stimulator assembly of FIG. 43 in a second configuration.
Figure 47:
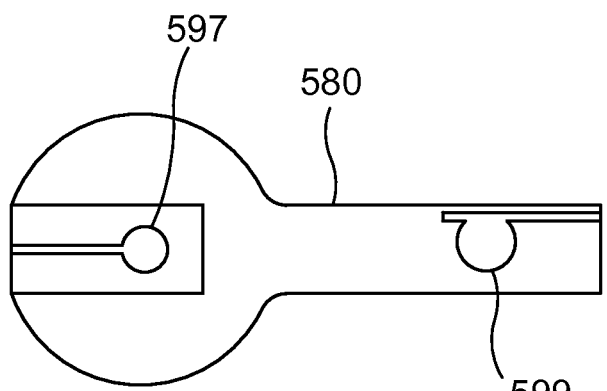

In its second configuration, the substrate 580 has a second area less than the first area (see, e.g., FIGS. 46-47). Similarly stated, when the substrate 580 is in its second (or folded) configuration, the substrate 580 occupies a second surface area and/or defines a second "footprint" that is smaller than the first "footprint." When the substrate 580 is in its second configuration, the electrodes 597, 599 and at least a portion of the electrical circuit 585 each face a second direction different than the first direction, as illustrated in FIGS. 45-46. For example, when the substrate 580 is in its second configuration and the substrate is positioned horizontally, the electrodes 597, 599 and the portion of the electrical circuit 585 can be characterized as facing "down," or towards the bodily tissue, while the remaining portion of the electrical circuit remains facing "up," or away from the bodily tissue. The substrate 580 can be moved from its first configuration to its second configuration, for example, by folding under at least one of tab portion 596 or tab portion 598, as shown in FIGS. 46-47, respectively. Because the substrate 580 is flexible, the substrate is not damaged (e.g., cracked, broken, or creased) when the at least one of the tab portions 596, 598 is folded under. Because the electrodes 597, 599 and the electrical circuit 585 are formed on a first side 581 of the substrate 580, manufacturing of the substrate 580 is more easily accomplished. For example, in some embodiments, the electrodes 597, 599 and/or electrical circuit 585 can be formed by an electrically conductive ink printed onto the first side of the substrate 580.

Figure 44:
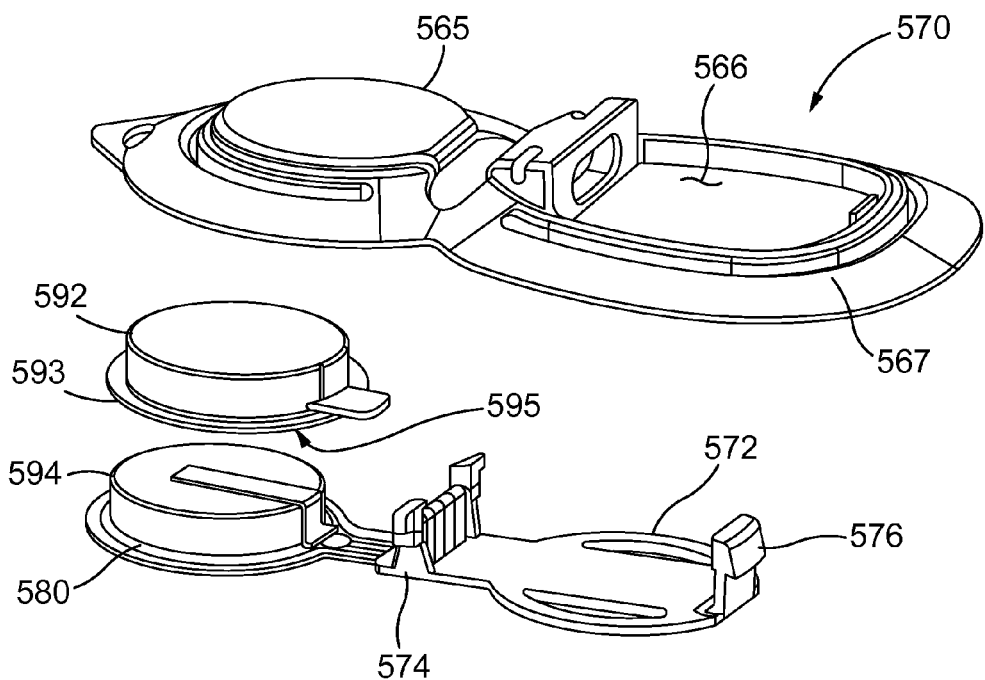
FIG. 44 is an exploded perspective view of the stimulator assembly of FIG. 43.

As illustrated in FIG. 44, the power source 594 is coupled to the first side 581 of the substrate 580. The power source 594 can be any suitable source of power for providing power to the electronic device, including any source of power shown and described herein. For example, the power source 594 can be a lithium battery, a rechargeable battery or the like. In some embodiments, the power source 594 provides enough power for approximately one week of standard use by a patient. In other embodiments, the power source 594 provides power for a longer period of time.

The casing 592 includes a rim 593 and defines a cavity (not shown, but indicated by arrow 595). The power source 594 is received in the cavity 595 of the casing 592. The rim 593 of the casing 592 is coupled to the substrate 580 to form a seal configured to substantially prevent the passage of moisture between the rim 593 of the casing 592 and the substrate 580. In this manner, the casing 592 substantially prevents entry of moisture into the cavity 593, and thus onto the power source 594 and/or the portion of the electrical circuit 585 coupled to the power source. As such, the casing 592 can limit a short-circuit of the power source 594 caused by exposure to moisture during the patient's daily activities, including bathing, perspiring, or swimming.

The electrical circuit 585 is configured to electrically couple each of the power source 594 and the electrodes 597, 599 to the electronic device. Each electrode 597, 599 is configured to contact a bodily tissue (either directly or via a secondary electrode), and to convey an electrical current between the electronic device and the bodily tissue. In some embodiments, at least one electrode 597, 599 can be associated with a hydrogel electrode. For example, a hydrogel electrode can be bonded to the substrate surrounding the perimeter of the at least one electrode 597, 599 such that the hydrogel electrode is disposed over and in electrical communication with the at least one electrode 597, 599.

Figure 43:
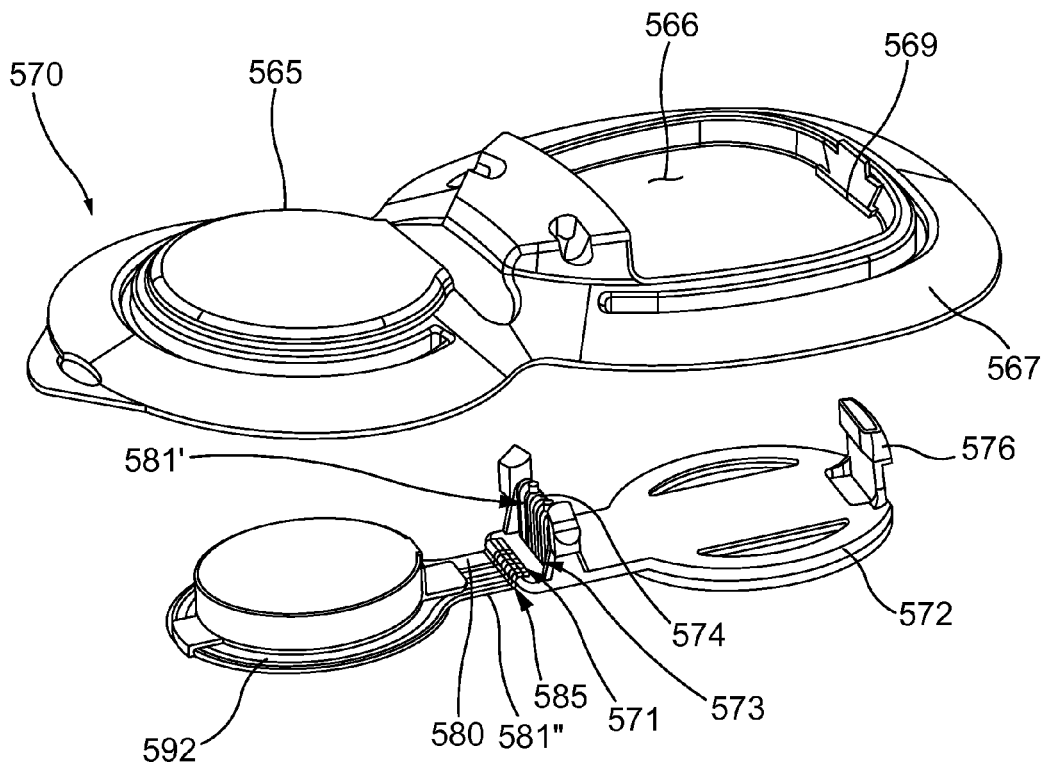
FIG. 43 is an exploded perspective view of a stimulator assembly according to an embodiment.

The coupling member 572 is coupled to the flexible substrate 580. More particularly, the coupling member 572 defines a first slot 571 and a second slot 573 different than the first slot. As illustrated in FIG. 43, at least a first portion of the substrate 580 is disposed within the first slot 571, and at least a second portion of the substrate is disposed within the second slot 573. In some embodiments, the coupling member 572 is substantially rigid, and therefore provides support to the flexible substrate 580. In some embodiments, the coupling member 572 can be similar in many respects to the base 372 described above with respect to the stimulation system 370.

The coupling member 572 also includes a connective member 574 and a protrusion 576. The substrate 580 is coupled to the connective member 574 such that a first portion 581' of the first side 581 of the substrate 580 is non-parallel to a second portion 581" of the first side of the substrate, as illustrated in FIG. 43. A portion of the electrical circuit 585 is disposed on the second portion 581" of the first side 581 of the substrate 580. Thus, the portion of the electrical circuit 585 is disposed proximate to a portion of the electronic device when the electronic device is coupled to the stimulation system 570, as described in more detail herein.

The coupling member 572 is configured to receive at least a portion of the electronic device in an area between the connective member 574 and the protrusion 576. The protrusion 576 of the coupling member 572 is configured to releasably couple the electronic device to the substrate 580. In some embodiments, the protrusion 576 is configured to releasably engage a recess of the electronic device (e.g., as shown and described above with respect to protrusion 476 and stimulus generator 490).

The housing 565 can be similar in many respects to housing 465 described herein. The housing 565 is disposable over at least a portion of the substrate 580. The housing includes a receiving portion 566 and defines an opening 569. The receiving portion 566 is configured to receive at least a portion of the electronic device. In some embodiments, the receiving portion 566 is defined by a surface 567 of the housing. The opening 569 of the housing 565 is configured to receive the protrusion 576 of the coupling member 572. In this manner, the protrusion 576 is configured to releasably engage the recess of the electronic device when the electronic device is disposed in the receiving portion 566 of the housing 565, and the protrusion 576 is received in the opening 569 defined by the housing.

In use, when the electronic device is received in the receiving portion 566 of the housing 565, the electronic device is placed in electrical communication with the electrical circuit 585. As such, the power source 594 can provide power to the electronic device such that the electronic device can generate an electrical current. The electrical current generated by the electronic device is transmitted from the electronic device to the electrical circuit 585. The electrical current is then transmitted from the electrical circuit 585 to the electrodes 597, 599. The electrodes 597, 599 convey the electrical current to the bodily tissue, thereby providing stimulation to the bodily tissue. In some embodiments, the electrodes 597, 599 are also configured to receive the electrical current from the bodily tissue, and to transmit the electrical current to the electronic device via the electrical pathway. In some embodiments, the stimulation system 570, or a portion thereof, is disposable. For example, the stimulation system 570 can be disposed of once the power source 594 is depleted and/or once the hydrogel electrode is no longer suitable for use (e.g., after approximately two weeks of continuous use). The usable life of the hydrogel electrode can be extended, however, if the electrode is stored properly when not in use (e.g., by applying a liner foil to the electrode to protect the hydrogel from humidity changes).

Figure 54:
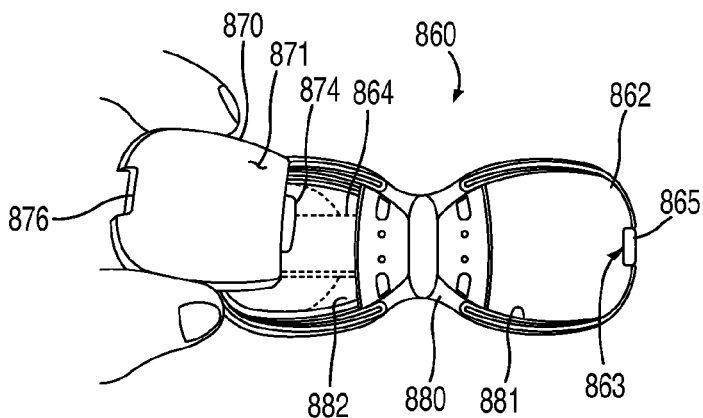
FIGS. 54-55 are top views of a stimulator assembly according to an embodiment in a first configuration and a second configuration, respectively.

In some embodiments, however, the power source is removable and/or replaceable, for example when the power source is low or depleted after use. As illustrated in FIG. 54, a stimulator assembly 860 according to an embodiment is configured to transmit electrical stimulation to a body of a patient and includes a flexible housing 880, a stimulus generator 862, and a removable power source 870.

The stimulus generator 862 can be similar in many respects to the stimulus generator 490, described above. The housing 880 includes a first receiving portion 881, which is configured to receive a portion of the stimulus generator 862. The stimulus generator 862 can be removably coupled to the housing 880 in any suitable manner described herein. For example, the stimulus generator 862 can be coupled to the housing 880 when the portion of the stimulus generator 862 is received in the first receiving portion 881 and a protrusion 865 of a base (not shown) of the stimulator assembly 860 engages a recess 863 of the stimulus generator.

The housing 880 defines a second receiving portion 882, which is configured to receive a portion of the power source 870, different than the first receiving portion 881. The receiving portions 881, 882 can be similar in many respects to receiving portion 466 described above. For example, the second receiving portion 882 defines a first opening (not shown in FIGS. 54-55) that is configured to receive a protrusion 874 of the power source 870. The protrusion 874 of the power source 870 can include, for example, one or more electrical contacts configured to place the power source 870 in electrical communication with other portions the stimulator assembly 860 (e.g., the stimulus generator 862, an electrical pathway, an electrode). The electrical contacts can be any suitable mechanism for electrically coupling the power source 870 with other portions the stimulator assembly 860. In some embodiments, the electrical contacts are biased to help retain the power source to the housing 880 and/or the stimulator assembly 860. For example, the electrical contacts can include a spring, an elastomer, or other suitable biasing mechanism.

The second receiving portion 882 also defines a second opening (not shown in FIGS. 54-55), which is configured to receive a protrusion 866 of a base 864 (shown in dashed lines in FIG. 54) of the stimulator assembly 860. The base 864 can be similar in many respects to the base 472, base 372 and/or the base 172 shown and described above.

The protrusion 866 of the base 864 is configured to couple the power source 870 to the housing 880 and other components of the stimulator assembly 860. Specifically, the protrusion 866 is configured to limit movement of the power source 870 with respect to the housing 880 when the power source is received in the receiving portion 882 of the housing.

Figure 55:
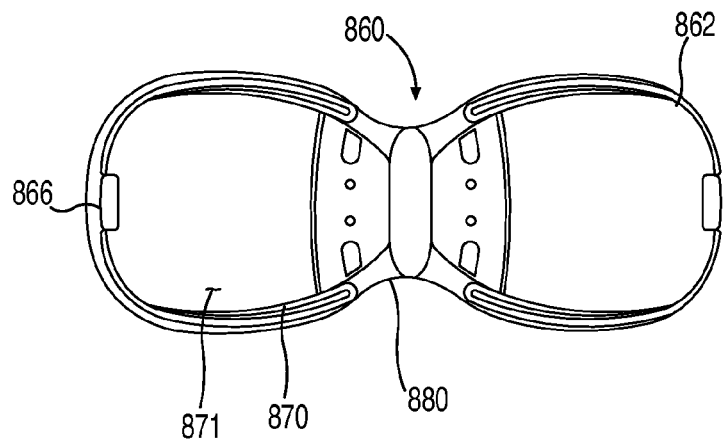

In use, when the power source 870 is received in the receiving portion of the housing 880 and the protrusion 874 of the power source is received in the first opening of the housing, the protrusion 866 of the base 864 engages a portion of the power source. For example, as illustrated in FIG. 54-55, the protrusion 866 engages a recess 876 defined by the power source 870 when the power source is received in the receiving portion 882 of the housing 880. In some embodiments, the protrusion 866 is resiliently biased towards the portion of the power source 870. In this manner, the protrusion 866 retains the power source 870 with respect to the housing 880 when the power source is received in the receiving portion 882 of the housing, and thus limits movement of the power source with respect to the housing 880. Said another way, the resistance that occurs by engagement of the protrusion 866 with the portion of the power source 870 facilitates coupling of the power source to the housing 880. The protrusion 866 is configured to release the power source 870 when the protrusion 866 is pushed, depressed, or otherwise moved by the operator (e.g., a physician, patient, or other user). Although the recess 876 is illustrated as being on an end of the power source 870 that is opposite to an end of the power source including the protrusion 874, in other embodiments, the recess (or other portion configured to engage protrusion 866) can be defined by a different portion of the power source.

Because the power source 870 is removable the operator can remove the power source from the stimulator assembly 860, for example, when the power source is depleted or otherwise insufficiently charged. After removal of the power source 870, a replacement power source of similar construct can be coupled to the stimulator assembly 860. In some embodiments, the power source 870 is also rechargeable. As such, at least a portion of the power source 870 is configured to be coupled to an external charging station, e.g., after removal from the stimulator assembly 860. While the power source 870 is being recharged, a second power source of similar construct can be used with the stimulator assembly 860, thus allowing for substantially uninterrupted treatment for the patient. Once the power source 870 is recharged to a sufficient power level and/or the secondary power source is depleted, the power source 870 can be re-coupled to the stimulator assembly 860.

When the power source 870 is received in the receiving portion 882 and the protrusion 874 of the power source is received in the first opening of the housing, the power source is electrically coupled to the stimulus generator 862. In some embodiments, the power source 870 is electrically coupled to the stimulus generator 862 via an electrical pathway (not shown in FIGS. 54-55) disposed on a substrate (not shown in FIGS. 54-55) of the stimulator assembly 860 in a similar manner as shown and described above with reference to substrate 380. More particularly, when the protrusion 874 of the power source 870 is received in the opening of the housing 880, the electrical contacts are placed in contact with the electrical pathway. The stimulus generator 862 is also in electrical connection with the electrical pathway, and thus is placed in electrical communication with the power source 870. In other words, the electrical pathway electrically couples the stimulus generator 862 to the power source 870. The housing 880 is configured to substantially maintain the power source 870 in electrical communication with the electrical pathway when the power source is received in the receiving portion 882 and the housing 880 is disposed about at least a portion of the substrate of the stimulator assembly 860. The housing 880 can be constructed of any suitable material, including those materials described above with respect to housing 465.

In some embodiments, the power source 870 includes a battery (not shown) and a casing 871. The battery is received in a cavity (not shown) of the casing 871. The casing 871 can be configured to substantially prevent the passage of moisture between an area external to the casing 871 and the cavity of the casing. In this manner, the casing 871 substantially prevents entry of moisture into the cavity, and thus onto the battery. As such, the casing 871 can limit a short-circuit of the battery caused by exposure to moisture during the patient's daily activities, including bathing, perspiring, or swimming. The casing 871 also can help prevent inadvertent disconnection of the battery caused by friction that occurs during the patient's daily activities, including walking or dressing.

In some embodiments, the casing 871 includes a panel (not shown) movable between an open position, in which the cavity is accessible from an area external to the casing, and a closed position, in which the cavity is sealed and/or otherwise inaccessible from an area external to the casing. When the panel of the casing 871 is in its open position, the battery can be removed from and/or inserted into the cavity, e.g., to remove and/or replace a depleted battery. In some embodiments in which the power source 870 is rechargeable, at least one of the casing 871 or the battery is configured to be coupled to an external charging station. The battery can be any suitable source of power described herein, including as described above with respect to battery 394.

Although the power source 870 has been illustrated and described herein as being coupled to the stimulator assembly 860 with protrusion 866 of the base 882, in other embodiments, the power source can be coupled to the stimulator assembly in a different manner, for example, as shown and described above with respect to apparatus 951.

Figure 48:
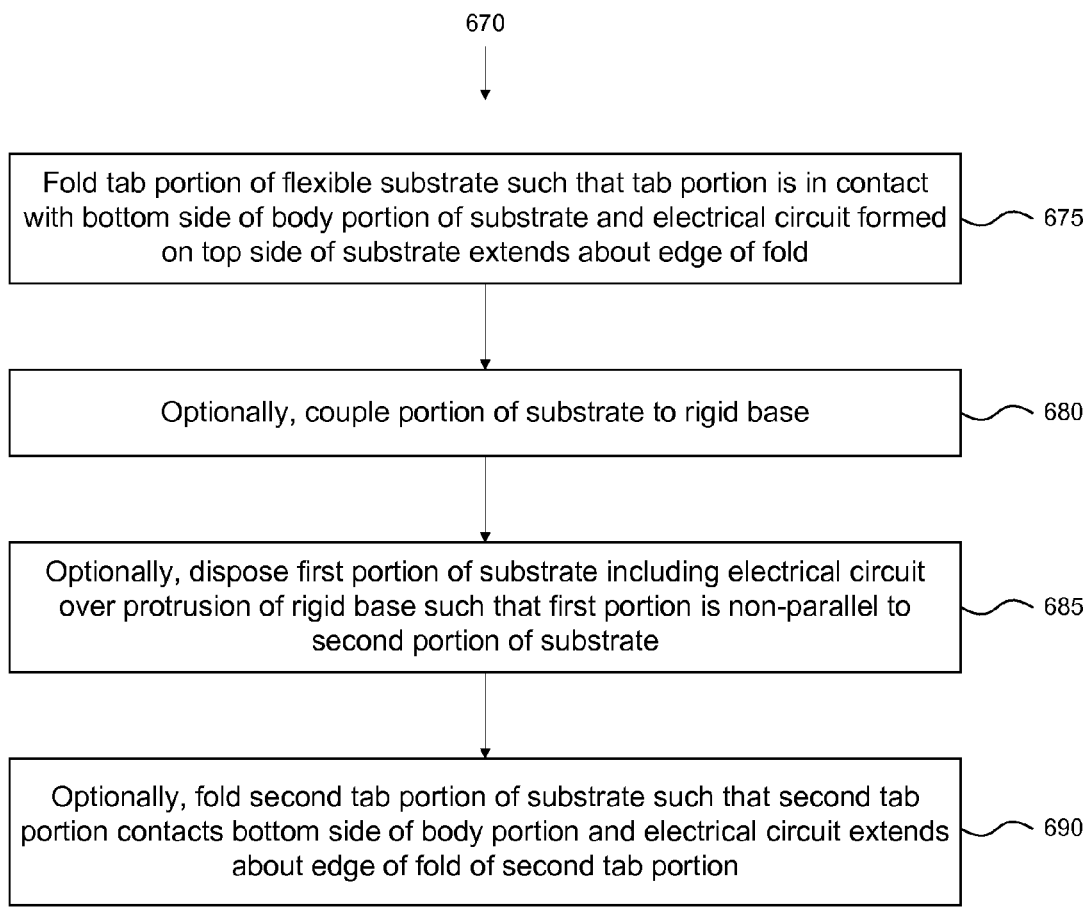
FIG. 48 is a flow chart of a method of assembling a portion of a stimulator system according to an embodiment.

FIG. 48 is a flow chart of a method 670 of assembling a portion of a stimulator assembly according to an embodiment. The method includes folding a tab portion of a flexible substrate such that the tab portion of the flexible substrate is in contact with a bottom side of a body portion of the flexible substrate and such that an electrical circuit formed on a top side of the flexible substrate extends about an edge of the fold, 675. The flexible substrate can be any substrate of the types shown and described herein (e.g., PCB 202, PCB 792, substrate 380, substrate 480, substrate 580). In some embodiments, the tab portion of the flexible substrate is bonded to the bottom side of the body portion of the flexible substrate. The electrical circuit can be formed on the top side of the flexible substrate in any manner shown and described herein. For example, the electrical circuit can be printed on the substrate. In another example, the electrical circuit can be partially embedded in the substrate such that a portion of the electrical circuit is exposed on a surface of the substrate.

In some embodiments, the method optionally includes coupling a portion of the flexible substrate to a rigid base, 680. The base can be, for example, any of the bases shown and described herein (e.g., base 372). The flexible substrate can be coupled to the rigid base in any suitable manner. In some embodiments, for example, at least a portion of the flexible substrate is woven through one or more openings defined by the rigid base (e.g., similar to the coupling of substrate 380 and base 372 shown and described above). The flexible substrate can, for example, be woven through a set of slots defined by the base.

In some embodiments, the method optionally includes disposing a first portion of the flexible substrate that includes the electrical circuit over a protrusion of the rigid base such that the first portion of the flexible substrate is non-parallel to a second portion of the flexible substrate, 685. For example, in some embodiments, the flexible substrate is disposed over the protrusion of the base similar to the disposal of substrate 380 over the protrusion 374 of the base 372 as shown and described above.

In some embodiments, the method optionally includes folding a second tab portion of the flexible substrate such that the second tab portion of the flexible substrate is in contact with the bottom side of the body portion of the flexible substrate and such that the electrical circuit extends about an edge of the fold of the second tab portion, 690. For example, in some embodiments, the second tab of the flexible substrate can be folded such that the substrate is in the second configuration as illustrated in FIGS. 45-47 and described above with respect to substrate 580.

Although the method 670 of assembling a portion of a stimulator assembly has been illustrated and described in one order, the activities can occur in a different order. For example, in some embodiments, the substrate is coupled to the rigid base prior to folding the tab portion of the flexible substrate. Furthermore, each activity is not required for assembling the portion of the stimulator assembly. For example, in some embodiments, a portion of the electrical circuit can be disposed on the top and bottom side of the second tab portion, wherein the second tab portion need not be folded to extend the electrical circuit about an edge of the fold of the second tab portion. Additionally, certain of the events may be performed concurrently in a parallel process when possible.

While various embodiments have been described above, it should be understood that they have been presented by way of example only, and not limitation. While the embodiments have been particularly shown and described, it will be understood that various changes in form and details may be made. For example, although the apparatus have been shown and described above as including a certain number of electrodes, in other embodiments, any suitable number of electrodes can be included. Further, elements of each embodiment described herein may be combined in any suitable manner with one or more elements of another embodiment described herein. For example, a hydrogel electrode may be selectively used with any of the foregoing apparatus, regardless if an embodiment was specifically described as including a hydrogel electrode. In another example, where an apparatus is shown and described herein as including a mechanical connector for connection to an external stimulator, in other embodiments, the apparatus can include a wireless connector for connection to the external stimulator.

Although various embodiments have been described as having particular features and/or combinations of components, other embodiments are possible having a combination of any features and/or components from any of the embodiments as discussed above. For example, a stimulation system according to an embodiment can include a base similar to the base 372 as described above and a folded substrate similar to the substrate 580 as described above.

Thus, the breadth and scope of the invention should not be limited by any of the above-described embodiments, but should be defined only in accordance with the following claims and their equivalents. The previous description of the embodiments is provided to enable any person skilled in the art to make or use the invention. While the invention has been particularly shown and described with reference to embodiments thereof, it will be understood by those skilled in the art that various changes in form and details may be made therein without departing from the spirit and scope of the invention.

Figure 49:
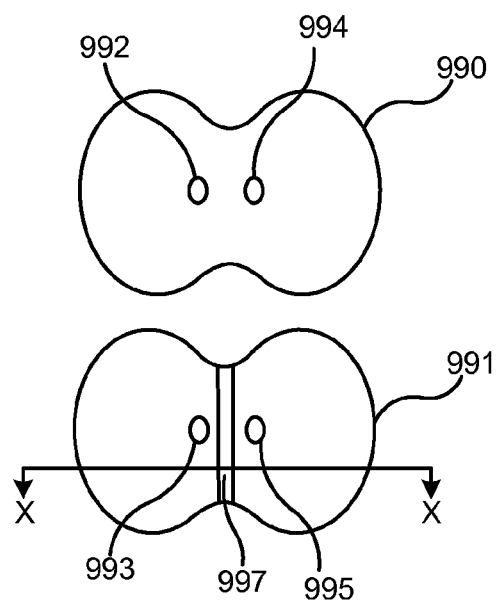
FIG. 49 is a top view of two experimental apparatus according to embodiments.
Figure 50:
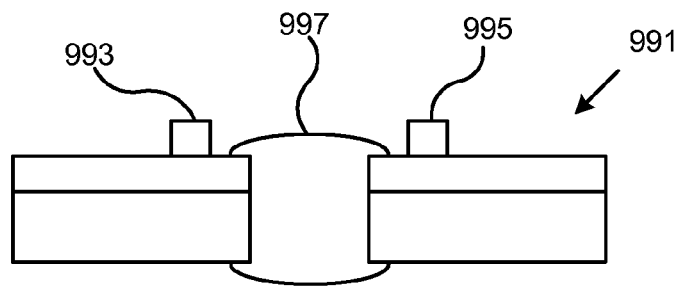
FIG. 50 is a cross-sectional view of an apparatus of FIG. 49 taken along line X-X.

An experiment was performed utilizing a first apparatus 990 and a second apparatus 991 according to an embodiment of the invention, as illustrated in FIG. 49, to estimate the leakage current when each of the first apparatus and the second apparatus is immersed in solutions encountered during daily activities. Apparatus 990 includes a first metal connector 992 and a second metal connector 994. Apparatus 991 was cut in the middle and the cut was filled with hot glue 997 to increase impedance between a first metal connector 993 and a second metal connector 995, as illustrated in FIGS. 49 and 50. Impedance of both direct current (DC) and alternating current (AC) was measured between the two metal connectors 992, 994 of the first apparatus 990. Impedance of both DC and AC was measured between the two metal connectors 993, 995 of the second apparatus 991 prior to submersion in the liquid. AC impedance was measured between the two metal connectors 992, 994 of the first apparatus 990 while the first apparatus was attached to skin of a patient. AC impedance was measured between the two metal connectors 993, 995 of the second apparatus 991 while the second apparatus was attached to the skin of the patient.

Figure 51:
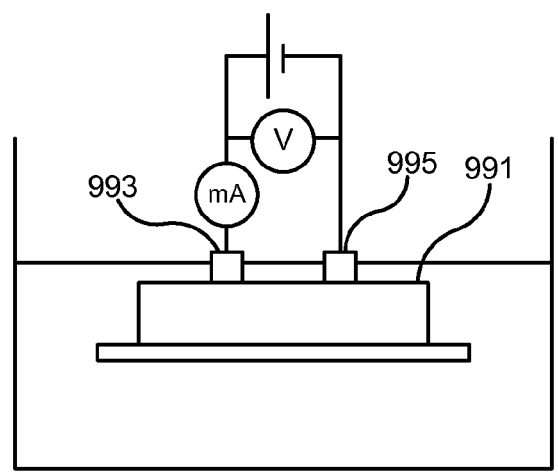
FIG. 51 is a front view of an apparatus of FIG. 49 partially immersed in a liquid.

Each of the first apparatus 990 and the second apparatus 991 was submerged in a liquid with a 3V Lithium coin battery attached to its respective metal connectors, as illustrated in FIG. 51 with reference to apparatus 991. The discharge current and voltage were each measured for each apparatus 990, 991 when the apparatus was submerged. Each of the discharge current, voltage and impedance were measured after removing the each apparatus 990, 991 from its respective liquid submersion. Additionally, each of the discharge current, voltage and impedance were measured after slight wiping of the each apparatus 990, 991. Each apparatus 990, 991 was then washed with tap water. These steps were performed for each of the following liquids: tap water, hot tub water, and saline solution. The discharge current showed an expected battery discharge, while AC impedance may represent leakage of the stimulation current on the patch rather than through bodily tissue. All AC impedance measurements were performed at 1 KHz. The results are shown in Table 1, below.

The results indicate that daily use of a bath or hot tub for 20 minutes drains 0.5-0.7 mAh per use (or 3.5-4.9 mAh per week). Assuming that the apparatus 991 incorporates a power source similar to a cr2032 coin lithium battery (225 mAh capacity), this drain is insignificant. A daily swim in ocean water for 20 minutes will drain ~3.3 mAh per day (or ~21 mAh per week), which is insignificant when compared to the suggested power source capacity. Further, the current drain during the drying period of 1 hour (for apparatus 990) is less than 1 mA per use (7 mAh per week) and does not add significant discharge compared with the power source capacity. After removal from the liquid, apparatus 991, which has a hydrophobic plastic barrier (similar to barrier 218 described above) ensures significantly lower power source discharge current compared to apparatus 990, which lacks a barrier. A significant amount of electrical current escapes via apparatus 990 and would not be expected to reach the body when apparatus 990 is exposed to liquid. However, apparatus 991 would be expected to divert most of the electrical current to the body, if wiped.

TABLE 1

Effects of Various Liquids on the Apparatus*

| | Apparatus 990 | | Apparatus 991 | |
|---|---|---|---|---|
| | Battery current | Impedance | Battery leakage | Impedance |
| Submersion in tap water | 1.5 mA | | 1.6 mA | |

TABLE 1-continued

Effects of Various Liquids on the Apparatus*

| | Apparatus 990 | | Apparatus 991 | |
|---|---|---|---|---|
| | Battery current | Impedance | Battery leakage | Impedance |
| Removal from tap water | 0.6 mA | 2.0 Kohm 27 nF | 0.1 mA | ∞ Kohm 49 pF |
| After wiping | 0.3 mA | 300 Kohm 2.0 nF | >0.1 mA | ∞ Kohm 30 pF |
| Submersion in hot tub water | 2 mA | | 2.2 mA | |
| Removal from hot tub water | 0.8 mA | 2.0 Kohm 13 nF | 0.07 mA | 1.7 Kohm 1.2 nF |
| After wiping | 0.5 mA | 90 Kohm 1.0 nF (130 Kohm after absorbing water with napkin) | >0.01 mA | 230 Kohm 128 pF |
| Submersion in saline solution | 9 mA | | 10 mA | |
| Removal from saline solution | 0.4 mA | 0.34 Kohm 212 nF | 0.04 mA | 3.5 Kohm 1.7 nF |
| After wiping | 0.3 mA | 0.5 Kohm 134 nF | >0.01 mA | 230 Kohm 94 nF |

*Before submersion, DC impedance approached infinity; AC impedance R approached infinity, C = pF; Impedance on the skin (AC) R = 8.3 Kohm, C = 36 nF. Battery voltage (when connected to the immersed patch) was 2.8-2.9 v.

What is claimed is:

1. An apparatus, comprising:
a substantially rigid base having a protrusion and defining a plurality of openings, each opening of the plurality of openings configured to receive therethrough a portion of the flexible substrate, the base configured to be coupled to an electronic device; and
a flexible substrate having a first surface and a second surface and including an electrical circuit configured to electronically couple the electronic device to at least one of an electrode, a battery, or an antenna, the flexible substrate coupled to the base such that a first portion of the second surface is in contact with the protrusion, a second portion of the second surface is non-parallel to the first portion, at least a third portion of the flexible substrate is disposed within a first opening of the plurality of openings, at least a fourth portion of the flexible substrate is disposed within a second opening of the plurality of openings, the first opening different than the second opening, the substrate having a first configuration in which the substrate has a first area and a second configuration in which the substrate has a second area less than the first area, the electrical circuit configured to electrically couple the electronic device to the electrode, the electrode facing a first direction when the substrate is in its first configuration, the electrical circuit facing the first direction when the substrate is in its first configuration, each of the electrode and a portion of the electrical circuit facing a second direction different than the first direction when the substrate is in its second configuration.

2. The apparatus of claim 1, wherein the first opening is defined by a first end of the base, the base including a second protrusion extended from a second end of the base different than the first end.

3. The apparatus of claim 1, wherein the protrusion of the base is extended from a portion of the base disposed between the first opening of the plurality of openings and the second opening of the plurality of openings.

4. The apparatus of claim 1, wherein:
a first portion of the first surface of the flexible substrate includes at least a portion of the electrical circuit, the portion of the electrical circuit configured to be in electrical communication with an electrical contact disposed on a first portion of the electronic device; and
the base includes a second protrusion configured to engage a second portion of the electronic device when the electronic device is coupled to the base, the second portion of the electronic device different than the first portion of the electronic device.

5. The apparatus of claim 1, further comprising:
a hydrogel electrode coupled to the second surface of the substrate, the substrate further including a conductive region electrically coupled to the electrical circuit and a plurality of non-conductive regions disposed within the conductive region and configured to facilitate retention of the hydrogel electrode with respect to the second surface of the substrate.

6. The apparatus of claim 1, further comprising:
a flexible housing configured to be disposed about at least a portion of at least one of the base and the flexible substrate, the housing including a receiving portion configured to receive at least a portion of the electronic device, the receiving portion defining an opening configured to receive a protrusion of the electronic device when the electronic device is received in the receiving portion such that the electronic device is electrically coupled to the battery.

7. The apparatus of claim 6, wherein a portion of the housing is configured to form a substantially fluid-tight seal proximate to the receiving portion when at least the portion of the electronic device is received in the receiving portion.

8. The apparatus of claim 6, wherein the housing is configured to substantially maintain the electronic device in electrical communication with the electrical circuit of the substrate when the electronic device is received in the receiving portion.

9. The apparatus of claim 1, further comprising:
a housing configured to be disposed over a portion of the substrate and a portion of the base, a surface of the housing defining a recess configured to receive therein at least a portion of the electronic device.

10. The apparatus of claim 1, wherein each of the electrode and the electrical circuit are disposed on a first side of the substrate when the substrate is in its first configuration.

11. The apparatus of claim 1, further comprising:
the battery; and
a casing including a rim and defining a cavity, the rim of the casing being coupled to the substrate to form a seal configured to substantially prevent the passage of moisture between the rim of the casing and the substrate, the battery being received in the cavity of the casing.

12. The apparatus of claim 1, wherein the protrusion of the base is a first protrusion, the base having a second protrusion different than the first protrusion, further comprising:
a housing disposable over at least a portion of the substrate, the housing including a receiving portion configured to receive at least a portion of the electronic device, the housing defining an opening configured to receive the second protrusion of the base,
the second protrusion of the base configured to releasably engage a recess of the electronic device when the electronic device is disposed in the receiving portion of the housing.

13. The apparatus of claim 1, wherein, when the flexible substrate is in its second configuration, a tab portion of the flexible substrate is folded such that the tab portion of the flexible substrate is in contact with a bottom side of a body portion of the flexible substrate and such that the electrical circuit formed on a top side of the flexible substrate extends about an edge of the fold, the flexible substrate configured to be coupled to a body.

14. The apparatus of claim 13, wherein the tab portion is a first tab portion, further comprising:
a second tab portion of the flexible substrate folded such that the second tab portion of the flexible substrate is in contact with the bottom side of the body portion of the flexible substrate and such that the electrical circuit extends about an edge of the fold of the second tab portion, when the flexible substrate is in its second configuration.

15. An apparatus, comprising:
a substantially rigid base having a protrusion and defining a plurality of openings, each opening of the plurality of openings configured to receive therethrough a portion of the flexible substrate, the base configured to be coupled to an electronic device; and
a flexible substrate having a first surface and a second surface and including an electrical circuit configured to electronically couple the electronic device to at least one of an electrode, a battery, or an antenna, the flexible substrate coupled to the base such that a first portion of the second surface is in contact with the protrusion, a second portion of the second surface is non-parallel to the first portion, at least a third portion of the flexible substrate is disposed within a first opening of the plurality of openings, at least a fourth portion of the flexible substrate is disposed within a second opening of the plurality of openings, the first opening different than the second opening, the flexible substrate including a tab portion folded such that the tab portion of the flexible substrate is in contact with a bottom side of a body portion of the flexible substrate and such that the electrical circuit formed on a top side of the flexible substrate extends about an edge of the fold, the flexible substrate configured to be coupled to a body.

16. The apparatus of claim 15, wherein the tab portion is a first tab portion, further comprising:
a second tab portion of the flexible substrate folded such that the second tab portion of the flexible substrate is in contact with the bottom side of the body portion of the flexible substrate and such that the electrical circuit extends about an edge of the fold of the second tab portion.

17. An apparatus, comprising:
a substantially rigid base having a protrusion and defining a plurality of openings, each opening of the plurality of openings configured to receive therethrough a portion of the flexible substrate, the base configured to be coupled to an electronic device;
a flexible substrate having a first surface and a second surface and including an electrical circuit configured to electronically couple the electronic device to at least one of an electrode, a battery, or an antenna, the flexible substrate coupled to the base such that a first portion of the second surface is in contact with the protrusion, a second portion of the second surface is non-parallel to the first portion, at least a third portion of the flexible substrate is disposed within a first opening of the plurality of openings, at least a fourth portion of the flexible substrate is disposed within a second opening of the plurality of openings, the first opening different than the second opening; and
a flexible housing configured to be disposed about at least a portion of at least one of the base and the flexible substrate, the housing including a receiving portion configured to receive at least a portion of the electronic device, the receiving portion defining an opening configured to receive a protrusion of the electronic device when the electronic device is received in the receiving portion such that the electronic device is electrically coupled to the battery.

18. The apparatus of claim 17, wherein a portion of the housing is configured to form a substantially fluid-tight seal proximate to the receiving portion when at least the portion of the electronic device is received in the receiving portion.

19. The apparatus of claim 17, wherein the housing is configured to substantially maintain the electronic device in electrical communication with the electrical circuit of the substrate when the electronic device is received in the receiving portion.

20. The apparatus of claim 17, wherein:
the protrusion of the base is a first protrusion, the base having a second protrusion different than the first protrusion,
the flexible housing defines an opening configured to receive the second protrusion of the base, and
the second protrusion of the base is configured to releasably engage a recess of the electronic device when the electronic device is disposed in the receiving portion of the housing.

* * * * *